(12) United States Patent
Pilon

(10) Patent No.: US 8,470,767 B2
(45) Date of Patent: Jun. 25, 2013

(54) METHODS AND COMPOSITIONS FOR THE REDUCTION OF NEUTROPHIL INFLUX AND THE TREATMENT OF BRONCHOPULMONARY DISPLASIA, RESPIRATORY DISTRESS SYNDROME, CHRONIC LUNG DISEASE, PULMONARY FIBROSIS, ASTHMA AND CHRONIC OBSTRUCTIVE PULMONARY DISEASE

(75) Inventor: Aprile L Pilon, Gaithersburg, MD (US)

(73) Assignee: Clarassance, Inc., Rockville, MD (US)

( * ) Notice: Subject to any disclaimer, the term of this patent is extended or adjusted under 35 U.S.C. 154(b) by 0 days.

(21) Appl. No.: 12/880,043

(22) Filed: Sep. 10, 2010

(65) Prior Publication Data

US 2011/0183887 A1 Jul. 28, 2011

Related U.S. Application Data

(63) Continuation of application No. 12/345,367, filed on Dec. 29, 2008, now Pat. No. 7,846,899, which is a continuation of application No. 11/378,798, filed on Mar. 16, 2006, now abandoned, which is a continuation-in-part of application No. 11/189,229, filed on Jul. 25, 2005, now abandoned, which is a continuation-in-part of application No. 09/835,784, filed on Apr. 13, 2001, now abandoned.

(51) Int. Cl.
*A61K 38/00* (2006.01)
*G01N 33/48* (2006.01)
*G01N 33/483* (2006.01)

(52) U.S. Cl.
USPC ............................................. 514/1.5; 436/63

(58) Field of Classification Search
None
See application file for complete search history.

(56) References Cited

U.S. PATENT DOCUMENTS

| | | |
|---|---|---|
| 4,691,009 A | 9/1987 | Palmer |
| 4,820,514 A | 4/1989 | Cummins |
| 4,917,826 A | 4/1990 | Johnson |
| 5,266,562 A | 11/1993 | Mukherjee |
| 5,354,269 A | 10/1994 | Goodheart |

(Continued)

FOREIGN PATENT DOCUMENTS

| | | |
|---|---|---|
| WO | 9608572 | 3/1996 |
| WO | 9640657 | 12/1996 |

(Continued)

OTHER PUBLICATIONS

Ray, M. et al. "Cloning and Characterization of the Mouse Clara Cell Specific 10 kDa Protein Gene Comparison of the 5'-Flanking Region With the Human Rat and Rabbit Gene", Biochemical and Biophysical Research Communications, vol. 197, No. 1: 163-171 (1993).

(Continued)

*Primary Examiner* — Cherie M Stanfield
(74) *Attorney, Agent, or Firm* — Henry J. Cittone; Cittone & Chinta LLP

(57) ABSTRACT

The present invention relates generally to the use of recombinant human CC10 (rhCC10), also known as recombinant human uteroglobin, for use as a therapeutic in the treatment of Respiratory Distress Syndrome (RDS), Bronchopulmonary dysplasia (BPD), chronic lung disease and/or pulmonary fibrosis, Asthma and Chronic Obstructive Pulmonary Disease (COPD). More particularly, the invention provides methods, including broadly the critical dosage ranges of rhCC10, which may be administered to safely and effectively treat the aforementioned conditions. The invention further provides a composition useful in administering rhCC10 to humans.

10 Claims, 8 Drawing Sheets

U.S. PATENT DOCUMENTS

| | | | |
|---|---|---|---|
| 5,470,885 | A | 11/1995 | Fuhrman |
| 5,482,930 | A | 1/1996 | Wei |
| 5,491,130 | A | 2/1996 | Roberts |
| 5,618,786 | A | 4/1997 | Roosdorp |
| 5,696,092 | A | 12/1997 | Patierno |
| 5,817,750 | A | 10/1998 | Ruoslahti |
| 6,066,724 | A | 5/2000 | Ni |
| 6,255,281 | B1 | 7/2001 | Pilon |
| 7,122,344 | B2 | 10/2006 | Pilon |
| 7,846,899 | B2 | 12/2010 | Pilon |
| 2002/0006640 | A1 | 1/2002 | Ni |
| 2002/0025510 | A1 | 2/2002 | Strongin |
| 2002/0160948 | A1 | 10/2002 | Pilon |
| 2002/0169108 | A1* | 11/2002 | Pilon ................................. 514/2 |
| 2002/0173460 | A1 | 11/2002 | Pilon |
| 2003/0008816 | A1 | 1/2003 | Pilon |
| 2003/0109429 | A1 | 6/2003 | Pilon |
| 2003/0207795 | A1 | 11/2003 | Pilon |
| 2004/0047857 | A1* | 3/2004 | Pilon et al. ................. 424/130.1 |
| 2005/0026139 | A1 | 2/2005 | Fang |
| 2005/0261180 | A1 | 11/2005 | Pilon |
| 2006/0025348 | A1 | 2/2006 | Pilon |
| 2006/0281681 | A1 | 12/2006 | Pilon |
| 2008/0064633 | A1 | 3/2008 | Pilon |
| 2009/0029917 | A1 | 1/2009 | Pilon |
| 2009/0197808 | A1 | 8/2009 | Pilon |
| 2009/0227025 | A1 | 9/2009 | Nichols |
| 2009/0253174 | A1 | 10/2009 | Serber |
| 2010/0183640 | A1 | 7/2010 | Pilon |
| 2011/0240012 | A1 | 10/2011 | Pilon |
| 2012/0231997 | A1 | 9/2012 | Pilon |

FOREIGN PATENT DOCUMENTS

| | | |
|---|---|---|
| WO | 9701627 | 1/1997 |
| WO | 9853846 | 12/1998 |
| WO | 9952493 | 10/1999 |
| WO | 00/72868 | 12/2000 |
| WO | 0109285 | 10/2001 |
| WO | 03003979 | 1/2003 |
| WO | 2007109118 | 9/2007 |
| WO | 2009140269 | 11/2009 |
| WO | 2011047065 | 4/2011 |

OTHER PUBLICATIONS

Rennard et al., "Production of Fibronectin by the Human Alveolar Macrophase: Mechanism for the Recruitment of Fibroblasts to Sites of Tissue Injury in Interstitial Lung Diseases" Proc. Natl. Acad. Sci. USA, 78(11): 7147-7151 (1988).

Ricci et al. (2004), Curr. Pharm. Des, 10(31): 3901-3911.

Robinson, D., "Macromolecular Transport in Rabbit Blastocysts: Evidence for a Specific Uteroglobin Transport System", Molecular and Cellular Endocrinology, 63: 227-237 (1989).

Ruoslahti et al, "Fibronectin and Its Receptors," Ann. Rev. Biochem, vol. 57, pp. 374-413 (1988).

Scheuer, W., "Phospholipase A2-regulation and inhibition," Klin Wochenschr, vol. 67, pp. 153-159 (1989).

Scopes R K (1994) Protein Purification Principles and Practice 3rd Edition (Cantor C R ed) pp. 270-277 Springer-Verlag, New York.

Shijubo, N. et al. "Serum and BAL Clara Cell 10 kDa Protein (CC10) Levels and CC10-Positive Bronchiolar Cells Are Decreased in Smokers", European Respiratory Journal, vol. 10: 1108-1114 (1997).

Shimizu et al. (1997), Biol. Pharm. Bull. 20(12)I 1219-1223.

Shin et al., Enhanced Production of Human Mini-Proinsulin in Fed-Batch Cultures at High Cell Density of *Esherichia coli* BL21(DE3)(pET-3aT2M2], Biotechnol. Prog. 1997, vol. 13, pp. 249-257, especially p. 249.

Singh et al, "Identification, Cellular Localization, Isolation, and Characterization of Human Clara Cell-Specific 10 KD Protein," J. Hist. Cyt, vol. 36, pp. 73-80 (1988b).

Singh, G. et al. "Mouse Clara Cell 10-kDa (CC10) Protein: cDNA Nucleotide Sequence and Molecular Basis for the Variation of Progesterone Binding of CC10 from Different Species", Experimental Lung Research vol. 19: 67-75 (1993).

Singh, G., et al., "Isolation and Amino Acid Composition of the Isotypes ofa Rat Clara Cell Specific Protein", Experimental Lung Research, 133299-309 (1987).

Sipes et al. (1993), J. Cell. Biol. 121(2); 469-477.

Steward el al. (2002), J. Mol Biol. 318i 935-940.

Stripp et al, "Clara cell secretory protein: a determinant of PCB bioaccumulation in mammals," Am. J. Physiol., 271 (Lung Cell Mol. Physiol. 15), pp. L656-L664 (1996).

Stripp et al, "Plasticity of airway cell proliferation and gene expression after acute naphthalene injury," Am. J. Physiol., vol. 269, pp. L791-L799 (1995).

Stripp, B. et al. "Structure and Regulation of the Murine Clara Cell Secretory Protein Gene", Genomics vol. 20: 27-35 (1994).

Stripp, B. et al., "cis-Acting Elements That Confer Lung Epithelial Cell Expression of the $CC_{10}$ Gene", Journal of Biological Chemistry, vol. 267, No. 21: 14703-14712 (1992).

Torkkeli et al., Uterine and lung uteroglobins in the rabbit. Two similar proteins with differential hormonal regulation Biochem Biophys Act. 1978, vol. 544, No. 3, pp. 578-592, especially pp. 580-581.

Tykka et al. A randomized double-blind study using CaNa2EDTA, a phospholipase A2 inhibitor, in the management of human acute pancreatitis. Scan. J. Gastroenterology, (Jan. 1985) 20 (1) 5-12.

Tykka et al. Phospholipase A2 inhibitors and their possible clinical use in the treatment of acute pancreatitis. Scand J Gastroenterol 1980;15(5):519-28, Abstract only.

Umland et al, "Structure of human Clara cell phopholipid-binding protein-ligand complex at 1.9 A resolution," Nature Struct. Biol., vol. 1, pp. 538-545 (1994).

Umland et al, "Twixt form and function," Nat. Struct. Biol, vol. 2, pp. 919-922 (1995).

UniProt Accession No. P10145 (IL8_Human. Jul. 1, 1989).

Vadas et al, "Potential therapeutic efficacy of inhibitors of.,.," Agents Actions, vol. 19, pp. 194-202 (1986).

Van Bisbergen et al, "Synthetic peptide from lipocortin 1 has no phospholipase inhibitory activity," FEBS Lett., vol. 247, pp. 293-297 (1989).

Van Winkle, L. et al., "Repair of Naphthalene-Injured Microdissected Airways In vitro" American Journal of Respiratory Cell and Molecular Biology, vol. 15: 1-8 (1996).

Vostal, J. et al. "Novel Peptides Derived From a Region of Local Homology Between Uteroglobin and Lipocortin-1 Inhibit Platelet Aggregation and Secretion", Biochemical and Biophysical Research Communications, vol. 165, No. 1: 27-36 (1989).

Watts et al., "Effect of Dexamethasone Therapy on Fibronectin and Albumin Levels in Lung Secretions of Infants with Bronchopulmonaw Dysplasia" J. Pediat. 121: 597-607 (1992).

Wolf et al. (1992), Hum MOI Genet 1(6)I 371-378.

Wu, C. et al. "Integrin Activation and Cytoskeletal Interaction Are Essential for the Assembly of a Fibronectin Matrix", Cell, vol. 83: 715-724 (1995).

Wuenschell, C. et al., "Embryonic Mouse Lung Epithelial Progenitor Cells Co-Express Immunohistochemical Markers of Diverse Mature Cell Lineages", The Journal of Histochemistry and Cytochemistry, vol. 44, No. 2: 113-123 (1996).

Zhang et al, "Modulation of Cell Surface Fibronectin Asembly Sites by Lysophosphatidic Acid," J. Cell Biol., vol. 127, pp. 1447-1459 (1994).

Zhang, Q. et al., "Cross-linking of the $NH_2$-Terminal Region of Fibronectin to Molecules of Large Apparent Molecular Mass", The Journal of Biological Chemistry vol. 271, No. 52: 33284-33292 (1996).

Pilon, Al, Pilon, A.L. The Development of Recombinant Human Uteroglobin/CC10 as a Therapeutic Agent in Inflammatory and Fibrotic Disease. Annals of the NYAS. vol. 293, pp. 280-299 (2000).

Farrow, J., Melby, J., Wiese, L., Lohnas, G., Welch, R., and Pilon, A.L. Binding of rhCC10 to Fibronectin and Its Effect on Cellular Adhesion. Annals of the NYAS. vol. 293, pp. 338-342 (2000).

Mukherjee, A.B., Kundu, G.C., Mantile-Selvaggi, G., et al. Uteroglobin: a novel cytokine? Cellular and Molecular Life Sciences 55:771-787, (1999).

Matthews, J.H., Pattabiraman, N., Ward, K.B., Mantile, G., Miele, L. and Mukherjee, A.B. Crystallization and characterization of the recombinant human Clara cell 10-kDa protein. Proteins 20:191-196 (1994).
Zhang, Z., et al. Human Uteroglobin Gene: Structure, Subchromosomal Localization, and Polymorphism. DNA & Cell Biol. 16:73-83 (1997).
Peri, A., Cordella-Miele, E., Miele, L. and Mukherjee, A.B. Tissue-specific expression of the gene coding for human Clara cell 10-kD protein, a phospholipase A2-inhibitory protein. J Clin Invest 92:2099-2109 (1993).
Bernard, A., et al. Human urinary protein 1: Evidence for identity with the Clara cell protein and occurrence in respiratory tract and urogenital secretions. Clin. Chim. Acta 207:239-249 (1992).
Jackson, P.J. and R. Turner. Purification and Partial Amino Acid Sequence of Human Urine Protein 1: Evidence for Homology with Rabbit Uteroglobin. J. Chromatog. 452:359-367 (1988).
Levin, S.W., et al. Uteroglobin inhibits phospholipase A2 activity. Life Sci. 38:1813-1819 (1986).
Mantile, G., Miele, L., Cordella-Miele, E., Singh, G., Katyal, S.L. and Mukherjee, A.B. Human Clara cell 10-kDa protein is the counterpart of rabbit uteroglobin. J Biol Chem 268:20343-20351 (1993).
Vasanthakumar, G., et al. Inhibition of phagocyte chemotaxis by potent phospholipase A2 inhibitory protein, Uteroglobin. Biochem. Pharmacol. 37:389-394 (1988).
Lesur, O., et al. Clara Cell Protein (CC-16) Induces a Phospholipase A2-mediated Inhibition of Fibroblast Migration In Vitro. Am. J. Respir. Crit. Care Med. 152:290-297 (1995).
Dierynck, I.A., et al. 1996. The human Clara cell protein: biochemical and biological characterization of a natural immunosuppressor. Multiple Schlerosis 1:385-387 (1996).
Leyton, J., et al. Recombinant human uteroglobin inhibits the in vitro invasiveness of human metastatic prostate tumor cells and the release of arachidonic acid stimulated by fibroblast-conditioned medium. Cancer Res., 54: 3696-3699 (1994).
Zhang, Z., et al. Severe Fibronectin-Deposit Renal Glomerular Disease in Mice Lacking Uteroglobin. 276:1408-1412 (1997).
Miele, L., Cordella-Miele, E., Mantile, G., Peri, A. and Mukherjee, A.B. Uteroglobin and uteroglobin-like proteins: the uteroglobin family of proteins. J Endocrinol Invest 17:679-692 (1994).
Johnston, C.J., et al. Altered Pulmonary Response to Hyperoxia in Clara Cell Secretory Protein Deficient Mice. Am. J. Respir. Cell Mol. Biol. 17:147-155 (1997).
Mango, G.W., et al. Clara cell secretory protein deficiency increases oxidant stress response in conducting airways. Am. J. Physiol. 275:L348-56 (1998).
Harrod, K.S., et al. Clara cell secretory protein decreases lung inflammation after acute virus infection. Am. J. Physiol. 275:L924-30 (1998).
Bernard, A.M., H.A. Roels, J.P. Buchet, and R.R. Lauwerys. Serum Clara cell protein: an indicator of bronchial cell dysfunction caused by tobacco smoking. Environ.Res. 66:96-104 (1994).
Bernard, A., et al. Clara cell protein in serum and bronchoalveolar lavage. Eur. Respir. J. 5:1231-1238 (1992).
Dhanireddy, R., T. Kikukawa, and A.B. Mukherjee. Detection of a rabbit uteroglobin-like protein in human neonatal tracheobronchial washings. BBRC 152:1447-1454 (1988).
Doyle, I.R., et al. Clearance of Clara Cell Secretory Protein 16 (CC16) and Surfactant Proteins A and B from Blood in Acute Respiratory Failure. Am. J. Respir. Crit. Care Med. 158:1528-1535 (1998).
Jorens, P., et al. Potential role of Clara cell protein, an endogenous phospholipase A2 inhibitor, in acute lung injury. Eur. Respir J. 8:1647-1653 (1995).
Hermans, C., and A. Bernard. Pneumoproteinaemia: a new perspective in the assessment of lung disorders. Eur. Respir. J. 11:801-803 (1998).
Van Vyve, et al. Protein content in bronchoalveolar lavage fluid of patients with asthma and control subjects. J. Allergy Clin. Immunol. 95:60-68 (1995).
Shijubo, et al. Serum Levels of Clara Cell 10-kDa Protein Are Decreased in Patients with Asthma. Lung 177:45-52 (1999).
Nomori, H., et al. Protein 1 (Clara Cell Protein) Serum Levels in Healthy Subjects and Patients with Bacterial Pneumonia. Am. J. Respir. Crit. Care Med. 152:746-750 (1995).
Dhanireddy, R., et al. Uteroglobin-like Protein in Premature Infants: Effect of Gestational Age. Ped. Res. 23:463A (1988).
Singh, G., and S.L. Katyal. Clara Cells and Clara Cell 10 kDa Protein (CC10). Am. J. Respir. Cell Mol. Biol. 17:141-143 (1997).
Dhanireddy, R., et al. Uteroglobin-like protein levels in premature infants on long term ventilator support. Ped. Res. 33:323A (1993).
Bernard, A., et al. Clara Cell Protein in Human Amniotic Fluid: A Potential Marker of Fetal Lung Growth. Ped. Res. 36:771-775 (1994).
Lopez de Haro, M.S., et al. Binding of retinoids to uteroglobin. FEBS Let. 349:249-251 (1994).
Singh, G. et al. Clara cell 10 kDa protein (CC10): comparison of structure and function to uteroglobin. Biochim. Biophys. Acta. 1039:348-355 (1990).
Peri, A., et al. Uteroglobin gene expression in the rabbit uterus throughout gestation and in the fetal lung: Relationship between uteroglobin and eicosanoid levels in the developing fetal lung. J. Clin. Invest. 96:343-353 (1995).
Davis, J.M. and Rosenfeld, W.N. Chronic Lung Disease. In: Neonatology:pathophysiology and Management of the Newborn, edited by Avery, G.B., Fletcher, M.A. and MacDonald, M.G. p. 453-477 (1994).
Whitsett, J.A., et al. Acute Respiratory Disorders. In: Neonatology:pathophysiology and Management of the Newborn, edited by Avery, G.B., Fletcher, M.A. and MacDonald, M.G. p. 429-452 (1994).
Stenmark, K., et al. Potential Role of Eicosanoids and PAF in the Pathophysiology of Bronchopulmonary Dysplasia. Am. Rev. Respir. Dis. 136:770-772 (1987).
Volovitz, B., et al. Relationship between leukotriene C4 and an uteroglobin-like protein in nasal and tracheobronchial mucosa of children. Implication in acute respiratory illnesses. Int. Arch Allergy Appl Immunol. 86:420-425 (1988).
Hermans, C., et al. Clara cell protein as a marker of Clara cell damage and bronchoalveolar blood barrier permeability. Eur. Respir. J. 13:1014-1021 (1999).
Lensmar, C., et al. Decreased pulmonary levels of the anti-inflammatory Clara cell 16 kDa protein after induction of airway inflammation in asthmatics. Cell. Mol. Life Sci. 57:976-981 (2000).
Lassus P, Nevalainen TJ, Eskola JU, Andersson S. Clara-cell secretory protein in preterm infants' tracheal aspirates correlates with maturity and increases in infection. Pediatr Pulmonol. 30(6):466-9 (2000).
Chen LC, Zhang Z, Myers AC, Huang SK. Cutting edge: altered pulmonary eosinophilic inflammation in mice deficient for Clara cell secretory 10-kDa protein. J Immunol. 167(6):3025-8 (2001).
Dierynck, I., et al. Potent inhibition of both human interferon-gamma production and biologic activity by the Clara cell protein, CC16. Am. J. Respir. Cell Mol. Biol. 12(2):205-10 (1995).
Shijubo N, Itoh Y, Yamaguchi T, Imada A, Hirasawa M, Yamada T, Kawai T, Abe S. Clara cell protein-positive epithelial cells are reduced in small airways of asthmatics. Am J Respir Crit Care Med. Sep. 1999;160(3):930-3.
Dhanireddy R, Kikukawa T, Mukherjee AB. Detection of a rabbit uteroglobin-like protein in human neonatal tracheobronchial washings. Biochem Biophys Res Commun. May 16, 1988;152(3):1447-54.
Khoor A, Gray Me, Singh G, Stahlman MT. Ontogeny of Clara cell-specific protein and its mRNA: their association with neuroepithelial bodies in human fetal lung and in bronchopulmonary dysplasia. J Histochem Cytochem. Dec. 1996;44(12):1429-38.
Miele L, Cordella-Miele E, Mantile G, Peri A, Mukherjee AB. Uteroglobin and uteroglobin-like proteins: the uteroglobin family of proteins. J Endocrinol Invest. Sep. 1994;17(8):679-92.
Johnston CJ, Mango GW, Finkelstein JN, Stripp BR. Altered pulmonary response to hyperoxia in Clara cell secretory protein deficient mice. Am J Respir Cell Mol Biol. Aug. 1997;17(2):147-55.
Mukherjee, A.B., E. Cordella-Miele, and L. Miele. 1992. Regulation of Extracellular Phospholipase A2 Activity: Implications for Inflammatory Diseases. DNA and Cell Biol. 11:233-243.

Nord M, Schubert K, Cassel TN, Andersson O, Riise GC. 2002. Decreased serum and bronchoalveolar lavage levels of Clara cell secretory protein (CC16) is associated with bronchiolitis obliterans syndrome and airway neutrophilia in lung transplant recipients. Transplantation. 73(8):1264-9.

Ramsay PL, DeMayo FJ, Hegemier SE, Wearden ME, Smith CV, Welty SE. 2001. Clara cell secretory protein oxidation and expression in premature infants who develop bronchopulmonary dysplasia. Am J Respir Crit Care Med. 164(1):155-61.

Geerts L, Jorens PG, Willems J, De Ley M, Slegers H. 2001. Natural inhibitors of neutrophil function in acute respiratory distress syndrome. Crit Care Med. 29(10)1920-4.

Wang SZ, Rosenberger CL, Espindola TM, Barrett EG, Tesfaigzi Y, Bice DE, Harrod KS. 2001. CCSP modulates airway dysfunction and host responses in an Ova-challenged mouse model. Am J Physiol Lung Cell Mol Physiol. 281 (5):L1303-11.

Miller TL, Shashikant BN, Melby JM, Pilon AL, Shaffer TH, Wolfson MR. Recombinant human Clara cell secretory protein in acute lung injury of the rabbit: effect of route of administration. Pediatr Crit Care Med. Nov. 2005;6 (6):698-706.

Miller TL, Shashikant BN, Pilon AL, Pierce RA, Shaffer TH, Wolfson MR. Effects of an intratracheally delivered anti-inflammatory protein (rhCC10) on physiological and lung structural indices in a juvenile model of acute lung injury. Biol Neonate. 2006;89(3):159-70. Epub Oct. 6, 2005.

Shashikant BN, Miller TL, Welch RW, Pilon AL, Shaffer TH, Wolfson MR. Dose response to rhCC10-augmented surfactant therapy in a lamb model of infant respiratory distress syndrome: physiological, inflammatory, and kinetic profiles. J Appl Physiol. Dec. 2005;99(6):2204-11. Epub Aug. 4, 2005.

Mandal AK, Ray R, Zhang Z, Chowdhury B, Pattabiraman N, Mukherjee AB. Uteroglobin inhibits prostaglandin F2alpha receptor-mediated expression of genes critical for the production of pro-inflammatory lipid mediators. J Biol Chem. Sep. 23, 2005;280(38):32897-904. Epub Aug. 1, 2005.

Mattsson J, Remberger M, Andersson O, Sundberg B, Nord M. Decreased serum levels of clara cell secretory protein (CC16) are associated with bronchiolitis obliterans and may permit early diagnosis in patients after allogeneic stem-cell transplantation. Transplantation. May 27, 2005;79(10):1411-6.

Welty SE. CC10 administration to premature infants: in search of the "silver bullet" to prevent lung inflammation. Pediatr Res. Jul. 2005;58(1):7-9. Epub May 5, 2005.

Benson M, Jansson L, Adner M, Luts A, Uddman R, Cardell LO. Gene profiling reveals decreased expression of uteroglobin and other anti-inflammatory genes in nasal fluid cells from patients with intermittent allergic rhinitis. Clin Exp Allergy. Apr. 2005;35(4):473-8.

Johansson S, Keen C, Ståhl A, Wennergren G, Benson M. Low levels of CC16 in nasal fluid of children with birch pollen-induced rhinitis. Allergy. May 2005;60(5):638-42.

Levine CR, Gewolb IH, Allen K, Welch RW, Melby JM, Pollack S, Shaffer T, Pilon AL, Davis JM. The safety, pharmacokinetics, and anti-inflammatory effects of intratracheal recombinant human Clara cell protein in premature infants with respiratory distress syndrome. Pediatr Res. Jul. 2005;58(1):15-21. Epub Mar. 17, 2005.

Ray R, Choi M, Zhang Z, Silverman GA, Askew D, Mukherjee AB. Uteroglobin suppresses SCCA gene expression associated with allergic asthma. J Biol Chem. Mar. 18, 2005;280(11):9761-4. Epub Jan. 27, 2005.

Yoshikawa S, Miyahara T, Reynolds SD, Stripp BR, Anghelescu M, Eyal FG, Parker JC. Clara cell secretory protein and phospholipase A2 activity modulate acute ventilator-induced lung injury in mice. J Appl Physiol. Apr. 2005;98 (4):1264-71. Epub Dec. 17, 2004.

Ye Q, Fujita M, Ouchi H, Inoshima I, Maeyama T, Kuwano K, Horiuchi Y, Hara N, Nakanishi Y. Serum CC-10 in inflammatory lung diseases. Respiration. Sep.-Oct. 2004;71(5):505-10.

Hung CH, Chen LC, Zhang Z, Chowdhury B, Lee WL, Plunkett B, Chen CH, Myers AC, Huang SK. Regulation of TH2 responses by the pulmonary Clara cell secretory 10-kd protein. J Allergy Clin Immunol. Sep. 2004;114(3):664-70.

Mandal AK, Zhang Z, Ray R, Choi MS, Chowdhury B, Pattabiraman N, Mukherjee AB. Uteroglobin represses allergen-induced inflammatory response by blocking PGD2 receptor-mediated functions. J Exp Med. May 17, 2004;199 (10):1317-30.

Iannuzzi MC. Clara cell protein in sarcoidosis: another job for the respiratory tract protector? Am J Respir Crit Care Med. Jan. 15, 2004;169(2):143-4.

Nosratabadi AR, Ljungman AG, Lindahl M, Welch R, Pilon A, Tagesson C. Clara cell 10-KDA protein inhibits endotoxin-induced airway contraction in isolated perfused rat lungs. Exp Lung Res. Oct.-Nov. 2003;29(7):455-73.

Ramsay PL, Luo Z, Major A, Park MS, Finegold M, Welty SE, Kwak I, Darlington G, Demayo FJ. Multiple mechanisms for oxygen-induced regulation of the Clara cell secretory protein gene. FASEB J. Nov. 2003;17(14):2142-4. EPUB Sep. 18, 2003.

Wang SZ, Rosenberger CL, Bao YX, Stark JM, Harrod KS. Clara cell secretory protein modulates lung inflammatory and immune responses to respiratory syncytial virus infection. J Immunol. Jul. 15, 2003;171(2):1051-60.

Chandra S, Davis JM, Drexler S, Kowalewska J, Chester D, Koo HC, Pollack S, Welch R, Pilon A, Levine CR. Safety and efficacy of intratracheal recombinant human Clara cell protein in a newborn piglet model of acute lung injury. Pediatr Res. Oct. 2003;54(4):509-15. Epub Jun. 18, 2003.

Shijubo N, Kawabata I, Sato N, Itoh Y. Clinical aspects of Clara cell 10-kDa protein/ uteroglobin (secretoglobin 1A1). Curr Pharm Des. 2003;9(14):1139-49. Review.

Angert et al., CC10 reduces inflammation in meconium aspiration syndrome in newborn piglets, Pediatric Res. 2007 vol. 62, No. 6 pp. 684-688.

Yoshikawa S, Miyahara T, Reynolds SD, Stripp BR, Anghelescu M, Eyal FG, Parker JC. Clara cell secretory protein and phospholipase A2 activity modulate acute ventilator-induced lung injury in mice. J Appl Physiol. Apr. 2005;98 (4):1264-71.

Castro et al., Attenuation of Pulmonary Neuroendocrine Differentiation in Mice Lacking Clara Cell Secretory Protein, vol. 80, No. 10, p. 1533 (2000).

Kim et al., IL-13-induced Clara cell secretory protein expression in airway epithelium: role of EGFR signaling pathway, AJP—Lung 283:67-75, 2002. First published Feb. 22, 2002.

Liu et al, Gene expression profiles in human nasal polyp tissues studied by means of DNA microarray, J Allergy Clin Immunol, Oct. 2004 pp. 783-790.

Magdaleno et al, Interferon-gamma regulation of Clara cell gene expression: in vivo and in vitro, Am. Phys. Soc. 1997 L1142-L1151.

Abman et al., "Pathophysiology and Treatment of Bronchopulmonary Dysplasia: Current Issues." Pediatric Clinics of North America, vol. 41 No. 2, pp. 277-315 (1994).

Akiyama et al., "Fibronectin and Integrins in Invasion . . . " Cancer and Metastasis Reviews. vol. 14, pp. 173-189 (1995).

Andersson et al., "Heterologous Expression of Human Uteroglobin/ Polychlorinated Biphenyl-binding Protein." J. Biol. Chem., vol. 269 pp. 19081-19087 (1994).

Aoki et al., "Isolation of Human Uteroglobin from Blood Filtrate." Mol. Hum. Reprod., vol. 2, pp. 489-497 (1996).

Assmann et al., "Familial Glomerulonephritis Characterized by Massive . . . " Am. J. Kid. Dis., vol. 25, pp. 781-791 (1995).

Badcock, N. R. et al., "False-Positive EMIT.RTM.-st.TM. Ethanol Screen with Post-Mortem Infant Plasma", Clinical Chemistry, vol. 38, No. 33: 434-435 (1992).

Bischoff, et al Biochemistry 3013464-3472, 1991 Purification and Biochemical Characterization of Recombinant alphal-antilrypsin variants expressed in E. coli.

Bowton et al. Phospholipase A2 and arachidonate increase in bronchoalveolar lavage fluid after inhaled antigen challenge in asthmatics. Am J. Respir Crit Care Med. Feb. 1997; 155(2):421-5.

Camussi et al., J. Exp Med. Mar. 1, 1990:171(3):913-27, Abstract.

Chan C-C et al: "Effects of antiflammins on endotoxin-induced uveitis in rats" Archives of Ophthalmology, vol. 109, No. 2, Feb. 1991, pp. 278-281, XP000960732.

Chiesa M. et al., "Significant increase in immunoregulaton; protein blastokinin/uteroglobin in IgA/firbronectin complexes in sera of patients with IgA nephropathy", Nephrology Dialysis Transplantation, vol. 15, No. 9, 2000, p. A39 XP000971167.

Chilton et al. 1996. Antigen-induced generation of lysophospholipids in human airways. J. Exp. Med. 183: 2235-2245.

ClaraGen Inc. Press Release. Jun. 2, 1997—Claragen Explores How Uteroglobin Can Prevent Neonatal Lung Disease.

Clement; Rev Mal Respir Jul. 1996; 13(3):243-9.

Dennis E.A. Potential phopholipase A2s involved in inflammatow diseases. Agents Actions Suppl. 1995. vol. 46, pp. 3539, see p. 35, full para. 2.

Edelson et al. Acute lung injury induced by phospholipase A2: 2, 7 Structural and funcational changes. Am. Rev. Respir. Dis. May 1991, vol. 143, pp. 1102-1109, see p. 1102, col. 1, full paragraph 1, paragraphs bridging cols. 1-2 and cols. 2-3, paragraph bridging pp. 1105-1106.

Gonzalez et al. Biding of uteroglobin to microsomes and plasmatic membranes. FEBS Letters. 1995, vol. 361, pp. 225-258, see p. 257, Figure 4.

UniProt Basic UniProtKB Entry Viewer, Uter_Human. Oct. 1, 1989, Accession No. P11684.

Guy J. et al. Surfactant-producing rabbit pulmonary alveolar type II cells synthesize and secrete an anti-inflammatory protein, uteroglobin. Biochemical and Biophysical Research Communications, vol. 189, No. 2, Dec. 15, 1992, pp. 662-669, XP002153573.

Information Hyperlinked Over Proteins—SCGB1A1—secretglobin, family 1A, member 1 (uteroglobin), Last accessed 44 Dec. 2007.

Jarjour et al. Antigen-induced airway inflammation in atopic subjects generates dysfunction of pulmonary surfactant. Am J Respir Crit Care Med. Jul. 1999;160(1)1336-41.

Konstan et al. Effect of high-dose ibuprofen in patients with cystic fibrosis. N Engl J Med. Mar. 30, 1995;332 (13):848-54.

Kundu et al. Recombinant human uteroglobin suppresses cellular invasiveness via a novel class of high-affinity cell surface binding site, Proc. Natl. Acad. Sci U.S.A. Apr. 2, 1996, vol. 93, No. 7, pp. 2915-2919, see p. 2915. para. bridging cols. 1-2.

Lindhal et al., "Demonstration of different forms of lipocortin-1 and Clara cell protein-16 in human nasal and bronchoalveolar lavage fluids", Electrophoresis 20: 881-890 (1999).

Liu et al. Pulmonary surfactant given prophylactically alleviates an asthma attack in guinea-pigs. Clin Exp Allergy. Mar. 26, 1996; (3):270-5.

Lloret, S. et al., "Effect of Nonapeptide Fragments of Uteroglobin and Lipocortin I on Oedema and Mast Cell Degranulation", European Journal of Pharmacology vol. 264: 379-384 (1994).

Itoh et al. (1993), J Clin Lab Anal 7 (6): 394-400.

Lunardi-Iskandar, Y., et al. "Effects of a Urinary Factor from Women in Early Preganancy of HIV I, SID and associated Disease", Nature Medicine, vol. 4, No. 4, 428-434 (1998).

Makrides, Strategies for Achieving High-Level Expression of Genes in *Escherichia coli*, Microbiological Reviews, American Society for Microbiology, Washington, DC, US, vol. 60, No. 3, Sep. 1996, ISSN: 0146-0749 *p. 524*.

Manjunath, R. et al. "Inhibition of Thrombin-Induced Platelet Aggregation by Uteroglobin" Biochemical Pharmacology, vol. 36, No. 5-741-746 (1987).

Manjunath, R. et al., "Crosslinking of Uteroglobin by Transglutaminase" Biochemical and Biophysical Research Communications, vol. 121, No. 11 400-407 (1984).

MeSH Database, entry for "Cystic Fibrosis" [online] National Center for Biotechnology Information, National Library of Medicine, NIH, Apr. 8, 2008.

Miele, L. et al. "Novel Anti-Inflammatory Peptides From the Region of Higher Similarity Between Uteroglobin and Lipocortin I", Nature, vol. 335, No. 6192: 726-730 (1988).

Miele, L. et al., "High Level Bacterial Expression of Uteroglobin, A Dimeric Eukaryotic Protein with Two Interchain Disulfide Bridges, in its natural quaternary Structure" Journal of Biological Chemistry, vol. 265, No. 11: 6427-6435 (1990).

Miele, L., et al., "Uteroglobin: Structure, Molecular Biology, and New Perspectives on Its Function as a Phospholipase A.sub.2 Inhibitor" Endocrine Reviews, vol. 8, No. 4: 474-490 (1987).

Mihal, K., "One gene encoding three proteins with different functions," Am. J. Respir. Cell. Moi. Biol, vol. 5, pp. 1-3 (1991).

Mourot et al., Comparative Evaluation of Ultrafiltration Membranes for Purification of Synthetic Peptides, Separation Science and Technology, 1989, vol. 24, No. 5 & 6, pp. 353-367, especially pp. 353 and 354.

Mukerjee A B et al. "Could the Gene Coding for Human Uteroglobin (Clara Cell 10kDa Protein) be a candidate gene for Atopy?" American Journal of Human Genetics vol. 55 No. 3 p. A197 (1994).

Mukherjee et al., "Modulation of Cellular Response to Antigens by Uteroglobin and Transglutaminase" Adv. Exp. Med. Biol., 231:135-152 (1988).

Mukherjee, A. et al., "Phospholipase A.sub.2 Enzymes: Regulation and Physiological Role", Biochemical Pharmacology, vol. 48, No. 1: 1-10 (1994).

Nomori, H., et al. "Protein 1 and Clara Cell 10-kDa Protein Distribution in Normal and Neoplastic Tissued with Emphasis on the Respiratory System", Virchows Archives, vol. 424: 517-523 (1994).

Nord, M.—M et al "Calcium-Dependent Binding of Uteroglobin (PCB-BP/CCSP) Two Negatively Charged Fossil Liposomes" EFEBS Letters vol. 374: 403-406 (1995).

Okutani, R. et al., "Simple and High-Yield Purification of Urine Protein 1 Using Immunoaffinity Chromatography: Evidence for the identity of Urine Protein 1 and Human Clara Cell 10-Kilodalton Protein", Journal of Chromatography, vol. 577: 25-35 (1992).

Olson et al. Know your neighbors: three phenotypes in null mutants of the myogenic bHLH gene MRF4. Cell Apr. 1996 5;85(1):14.

Pattabiraman et al., Crystal Structure Analysis of Recombinant Human Uteroglobin and Molecular Modeling of Ligand Binding, Ann. NY, Acad. Sci. 2000, vol. 923, pp. 113-127.

Peri et al., "Expression of Clara Cell 10-kD Gene in the Human Endometrium and its Relationship to Ovarian Menstrual Cycle," DNA and Cell Biology, 13(5):495-503 (1994).

Peter, W., "Recombinant Rabbit Uteroglobin Expressed at High Levels in *E. coli* Forms Stable Dimers and Binds Progesterone", Protein Engineering, vol. 3: 61-66 (1989).

Peteres et al, "Clinical determinants of abnormalities in pulmonary functions in survivors of . . . ," Am. Rev. Respir. Dis., vol. 139, pp. 1163-1168 (1989).

Piomelli, D., "Arachidonic Acid in Cell Signaling", Current Opinion in Cell Biology, 5: 274-180 (1993).

R&D Systems, Quantikine assay for IL-8 (Oct. 2004).

Wang SZ, Rosenberger CL, Bao YX, Stark JM, Harrod KS, Clara cell secretory protein modulates lung inflammatory and immune responses to respiratory syncytial virus infection, J Immunol. Jul. 15, 2003;171(2):1051-60.

Ikegami M, Harrod KS, Whitsett JA, Jobe AH, CCSP deficiency does not alter surfactant homeostasis during adenoviral infection, Am J Physiol. Nov. 1999;277(5 Pt 1):L983-7.

Harrod KS, Mounday AD, Stripp BR, Whitsett JA, Clara cell secretory protein decreases lung inflammation after acute virus infection, Am J Physiol. Nov. 1998;275(5 Pt 1):L924-30.

Search Report and Written opinion for PCT/us2010/052527 dated Jan 5, 2011.

Hendrickson et al., Development of Lentiviral Vectors with Regulated Respiratory Epithelial Expression In Vivo, Am. J. Resp. Cell & Molec. Bio. 2007 37(4); 414-423, Tables 1&2.

Murakami et al. Mini-plasmin found in the epithelial cells of bronchioles triggers infection by broad spectrum influenza A viruses and Sendai virus. Eur. J. of Biochem. 2001, 268:2847-2855; p. 2853, col. 2, pra 1 to p. 2854 col. 1 para 3.

Endo et al., Growth of Influence A Virus in Primary, Differentiated Epithelial Cells Derived from Adenoids, Am. Soc. for Micro. 1996, 70(3):2055-2058; p. 2057.
Islam et al., Acquisition of Pathogenicity of a Newcastle Disease Virus Isolated from a Japanese Quail by Intracerebral Passage in Chickens, JP J. of Vet. Res. 1995 42(3-4):147-156; Abstract, Tables 3-5.

* cited by examiner

METHODS AND COMPOSITIONS FOR THE REDUCTION OF NEUTROPHIL INFLUX AND THE TREATMENT OF BRONCHOPULMONARY DISPLASIA, RESPIRATORY DISTRESS SYNDROME, CHRONIC LUNG DISEASE, PULMONARY FIBROSIS, ASTHMA AND CHRONIC OBSTRUCTIVE PULMONARY DISEASE

CROSS REFERENCE TO RELATED APPLICATIONS

This application is a continuation of application Ser. No. 12/345,367, filed Dec. 29, 2008, now U.S. Pat. No. 7,846,899, which is a continuation of application Ser. No. 11/378,798, filed Mar. 16, 2006, now abandoned, which is a continuation-in-part of application Ser. No. 11/189,229, filed Jul. 25, 2005, now abandoned, which is a continuation-in-part of application Ser. No. 09/835,784, filed Apr. 13, 2001, now abandoned. Each of the aforementioned applications and patent are incorporated herein by reference in their entirety.

FIELD OF THE INVENTION

The present invention relates to methods of reducing the influx of neutrophils into the lungs of a human. More specifically the present invention relates to methods of treating respiratory distress syndrome (RDS) bronchopulmonary dysplasia (BPD), chronic lung disease, pulmonary fibrosis, asthma and chronic obstructive pulmonary disease (COPD) in humans and compositions useful for the same. Yet more specifically, the present invention relates to methods of treating the above using recombinant human CC10 and compositions useful for the same.

BACKGROUND

The influx of neutrophils into the lung is known to be a cause of the destruction of functional lung tissue and the harmful symptoms of RDS, BPD, chronic lung disease, pulmonary fibrosis, asthma and COPD. Neutrophil influx is the migration of neutrophils from the blood into tissue in response to any type of irritation or injury to the tissue. In RDS, BPD, chronic lung disease and/or pulmonary fibrosis, asthma and COPD total cell influx and neutrophil influx results in damage to and destruction of pulmonary tissue, ultimately causing functional lung tissue to be replaced with non-functioning fibrotic tissue. Thus, neutrophil influx is ultimately responsible for causing pulmonary fibrosis to the lungs, which lead to damaged lung tissue and possibly death.

When circulating neutrophils are activated by chemical and cytokine signals released by damaged or irritated tissue, for example, by IL-8 from the lungs, they adhere to the walls of blood vessels in the damaged tissue, following the chemical and cytokine signal to the source, and migrate through the vascular endothelia and into the damaged lung. Neutrophils release many powerful enzymes, such as myeloperoxidase (MPO), an enzyme that chemically damages and modifies all proteins in its local vicinity, usually inactivating them. MPO damages local lung tissue and proteins, as well as those of the infectious agents. Neutrophils also release powerful proteases, such as elastase, that indiscriminately degrade host and pathogen proteins alike. Thus, activated neutrophils that migrate into the lungs in response to some irritation of the respiratory tract release non-specific destructive enzymes that damage the host's respiratory tissues, as well as any infectious agents present. These, and other, powerful non-specific destructive mediators released by neutrophils damage all cell types and destroy lung tissue, including breaking down the bronchiolar and alveolar structure, resulting in decreased lung function and respiratory distress. Local vascular structure is also damaged, resulting in increased vascular permeability and leakage of serum proteins into the lung and tracheal fluid, further impairing function.

This non-specific neutrophil response results in greater damage to respiratory tissue than the original irritant or infectious agent. Patients that develop respiratory symptoms or respiratory distress as a result of an exposure to an irritant such as an allergen, air-borne particulate matter, chemicals, or infectious agents often experience the worst symptoms after the irritant or infectious agent is cleared from the respiratory tract. Neutrophils are substantially responsible for this over-reaction.

Neutrophil influx to the lungs is measured in patients by counting the number of neutral-staining white cells per unit volume in tracheal fluids (referred to as tracheal aspirate fluid or TAF). Tracheal fluids are continuous with bronchial fluids, alveolar fluids, and nasal and sinus fluids. Tracheal fluid composition is representative of pulmonary fluids in the lower respiratory tract, as well as the upper respiratory tract (nasal and sinus fluid).

Cytokines, like IL-6 and 1L-8, are released by local epithelial cells, endothelial cells, and fibroblasts. The levels of cytokines, for example IL-6 and IL-8, are measured in lung fluids such as TAF and in plasma or serum. Cytokines are basic regulators of all neutrophil functions. Under normal conditions, neutrophils move along microvascular walls via low affinity interaction of selectins with specific endothelial carbohydrate ligands. However, during the inflammatory response, chemotactic factors and proinflammatory cytokines signal the recruitment of neutrophils (neutrophil influx) to sites of infection and/or injury. Neutrophils then penetrate the endothelial layer and migrate through connective tissue to sites of injury, for example the lungs, where they accumulate and adhere to extracellular matrix components such as fibronectin and/or collagen.

RDS affects 10% of all premature infants and only rarely affects those born at full-term. RDS also affects adults. The disease is caused by a lack of lung surfactant, a chemical that normally appears in mature lungs, or by tissue damage to the lungs from being on a mechanical ventilator and oxygen for a significant amount of time. Surfactant keeps the air sacs from collapsing and allows them to inflate with air more easily. In respiratory distress syndrome, the air sacs collapse and prevent the child from breathing properly. In infants, symptoms usually appear shortly after birth and become progressively more severe. If symptoms of RDS persist, the condition is considered BPD if a baby is dependent on artificially supplied oxygen at 36 weeks' postconceptional age (PCA—also known as post-conceptual age). In a child or adult, if symptoms of RDS persist, the condition is considered chronic lung disease and/or pulmonary fibrosis if the patient is dependent on artificially supplied oxygen following a respiratory distress episode.

BPD affects 20-60% of all premature, very low birth weight infants. BPD and RDS are associated with substantial morbidity and mortality as well as extremely high health care costs. Although the widespread use of intratracheally administered exogenous surfactant and antenatal steroid therapy has reduced the overall severity of BPD, the prevalence of this condition has increased with improved survival of very low birth weight infants. BPD is a multi-factorial disease process that is the end result of an immature, surfactant deficient lung that has been exposed to hyperoxia, mechanical ventilation and infection. Furthermore, it is well documented that increased concentrations of cytokines and cells present in the tracheal aspirate fluid of premature infants within the first few days of life are associated with the subsequent development of RDS and BPD. Still further it is known that higher levels of fibronectin are present in the tracheal fluid and lungs of patients suffering from RDS and BPD and thus it causes and contributes to respiratory distress. Thus, treating and preventing RDS and BPD by providing improved lung function during the first few days of life of a premature infant is critical to the long term survivability of the infant.

Asthma is a chronic lung condition characterized by difficulty in breathing. Symptoms include: wheezing, coughing shortness of breath and chest tightness. People with asthma have extra sensitive or hyperresponsive airways. The airways react by narrowing or obstructing when they become irritated. This makes it difficult for the air to move in and out. This narrowing or obstruction causes the symptoms of asthma. The narrowing or obstruction of the airways is caused by: airway inflammation (meaning that the airways in the lungs become red, swollen and narrow) or bronchoconstriction (meaning that the muscles that encircle the airways tighten or go into spasm)

COPD is a lung disease in which the lungs are damaged, making it hard to breathe. In COPD, the airways are partly obstructed, making it difficult to get air in and out of the lungs. Most cases of chronic obstructive pulmonary disease (COPD) develop after repeatedly breathing in fumes and other things that irritate and damage the lungs and airways, for example by smoking. The lungs and airways are highly sensitive to irritants. They cause the airways to become inflamed and narrowed, and they destroy the elastic fibers that allow the lung to stretch and then return to its resting shape. This makes breathing air in and out of the lungs more difficult. COPD may also be caused by a gene-related disorder called alpha 1 antitrypsin deficiency. Alpha 1 antitrypsin is a protein that inactivates destructive proteins. People with antitrypsin deficiency have low levels of alpha 1 antitrypsin; the resulting imbalance of proteins leads to the destruction of the lungs and COPD.

Symptoms common to RDS, BPD, chronic lung disease, pulmonary fibrosis, asthma and COPD include respiratory insufficiency (i.e. lungs unable to adequately oxygenate the blood and remove carbon dioxide), increased airway resistance, inflammation and fibrosis of the lungs. Each of these symptoms are substantially caused by excessive levels of neutrophils, 1L-6, 1L-8, and total cells in the tracheal fluid. Excess total protein in the tracheal aspirate fluid ("TAF") or bronchoalveolar lavage fluid ("BAL") is also associated with lung inflammation and fibrosis in RDS, BPD, chronic lung disease, pulmonary fibrosis, asthma and COPD.

Glucocorticoids, also known as corticosteroids, are powerful anti-inflammatory agents that are known to improved lung function, to reduce the incidence of BPD in premature infants, and to improve the symptoms of RDS, BPD, chronic lung disease and/or pulmonary fibrosis, asthma and COPD. However, they are not completely safe to use. There are dangerous, often life-threatening side effects associated with the use of glucocorticoids in infants, children and adults. In infants, corticosteroids are avoided in clinical practice because they cause growth retardation, disproportionate growth inhibition of the central nervous system and head, and severe neurological impairment. In children, normal growth is stunted, resulting in small stature, due to treatment with corticosteroids. And in adults, cardiovascular complications, including hypertension and stroke, are major side effects of corticosteroids. In all patients, corticosteroids lower the patient's immune function and leave them susceptible to infection of all types (bacterial, viral, fungal, etc.), sometimes resulting in a lethal infection. Thus, safety is a major consideration in the choice of anti-inflammatory agent used to treat, prevent or cure RDS, BPD, chronic lung disease and/or pulmonary fibrosis, asthma and COPD and their related respiratory symptoms, reduce the severity of asthma or allergy, and prevent the progression of existing chronic lung disease such as. COPD or the development of chronic lung disease such as BPD. It is a significant challenge to find an anti-inflammatory agent powerful enough to alleviate respiratory symptoms and which is safe to use.

Human CC10 (hereinafter CC10), also known as uteroglobin, is a small homodimeric secretory protein produced by mucosal epithelial cells. In humans, Clara cells, a type of mucosal epithelial cell located in the airways, are the main site of CC 10 production. CC10 also circulates in the blood and is excreted in urine. CC10 is known to have anti-inflammatory properties. CC10 inhibits secretory $PLA_2$, an enzyme that degrades surfactant and facilitates eicosanoid biosynthesis. Eicosanoids are a family of lipophilic compounds including prostaglandins, leukotrienes, thromboxanes, and other arachidonic acid metabolites.

Further information concerning rhCC10, its structure and methods of use is found in U.S. Pat. No. 6,255,281, its continuation-in-part, U.S. patent application Ser. No. 09/087, 210, and in the following U.S. Patent Application Publication Nos.: US 2002-0160948, US 2002-0160948, US 2003-0008816, US 2003-0109429, US 2003-0207795, US 2002-0173460, US 2002-0169108, US 2005-0261180, US 2004-0047857, and US 2006-0025348, all of which are incorporated by reference in their entirety.

Very low concentrations of CC10 have been found in the TAF or BAL of patients suffering from RDS, Asthma and COPD and BPD. For example, very low concentrations of CC10 have been found in the tracheal aspirate fluid (TAF) of ventilated premature infants suffering from BPD relative to normal levels. These infants are not yet able to produce enough natural CC10 on their own, and develop severe lung inflammation. Normally, the appearance of CC10 in the amniotic fluid dates from 16 weeks of gestation and increases as a function of gestational as well as postnatal age. CC10 concentrations in tracheal fluid, measured by determining the amount of CC10 protein in the tracheal aspirate fluid, of premature infants born at 28-32 weeks of gestation have been found to be 2-4 orders of magnitude less than those found in the tracheal sputum (a.k.a. tracheal fluid) of healthy adults. CC10 concentrations correlate in a negative fashion with the concentration of inspired oxygen required by preterm infants with BPD. That is, infants with lower CC10 in TAF require greater amounts of supplemental oxygen. In fact, not only are CC10 concentrations lower in tracheal fluid from infants who either died or developed BPD, but the limited amount of available CC10 was oxidized and demonstrated less immunoreactivity relative to controls.

Recombinant CC10 (recombinant human CC10) has not been previously used to treat patients, including preterm infants for a number of reasons. First, rhCC10 of sufficient purity has not been previously available. Nor was it known whether rhCC10 caused specific toxicity or triggered an immune response to endogenous CC10 when administered. Furthermore, CC10 is known to inhibit platelet aggregation, thus negatively impacting the ability of the blood to clot. CC10 is also known to suppress the immune system, which could lead to adverse patient consequences, render recipients more susceptible to infection, and prohibit its use in humans, including premature infants. It was not known what dosage or dosage range would avoid deleterious immunogenicity, specific toxicity, and inhibition of platelet aggregation and suppression of the immune system.

Furthermore, it was not known whether rhCC10 would cause significantly lower total protein concentrations in the tracheal fluids of patients or what dosage to administer to achieve significantly lower total protein concentrations in the tracheal fluid of patients, a necessary outcome in treating BPD.

Additionally, it was not known whether rhCC10 would cause significantly lower total cell, neutrophil, IL-6 or IL-8 levels in patients or which dosage to administer to achieve significantly lower neutrophil, IL-6 or IL-8 levels in patients, also a necessary outcome in treating RDS, BDP, chronic lung disease and/or pulmonary fibrosis, Asthma, and COPD.

As shown below, the prior technological difficulties in using CC10 to provide a safe, well-tolerated and effective treatment for RDS, BDP, chronic lung disease, pulmonary fibrosis, asthma, and COPD have been overcome.

OBJECTS OF THE INVENTION

The foregoing provides a non-exclusive list of the objectives achieved by the present invention:

It is a primary object of the invention to treat, cure or prevent RDS, BDP, chronic lung disease and/or pulmonary fibrosis, asthma, and COPD in humans.

It is a further object of the invention to treat, cure or prevent RDS, BDP, chronic lung disease and/or pulmonary fibrosis, asthma, and COPD in humans by reducing total cell counts, neutrophil counts, total protein concentration IL-6 levels and/or IL-8 levels in the serum or tracheal fluid, and therefore the lungs, of patients.

It is a further object of the invention to provide a safe, well-tolerated and effective dosage range which accomplishes the above objectives and does not significantly inhibit platelet aggregation, suppress the immune response or increase the frequency or severity of adverse events.

It is yet another object of the invention to provide a safe, well-tolerated and effective dosage which provides a substantially effective range of CC10 levels in patient serum, tracheal fluid and urine.

SUMMARY OF THE INVENTION

These and other objects, features and advantages are achieved by administering rhCC10 in a dosage range given at appropriate intervals, or in one dose to treat, cure or prevent RDS, BDP, chronic lung disease, pulmonary fibrosis, asthma, and COPD.

These and other objects, features and advantages are also achieved by administering rhCC10 in a dosage range given at appropriate intervals or in one dose where a patient shows one or more of the following: IL-6 levels below 200 pg/ml of tracheal aspirate fluid, IL-8 levels below 100 pg/ml in serum, total neutrophil cell counts below $20 \text{ cells} \times 10^4/\text{ml}$ of tracheal aspirate fluid, total cell counts below $50 \text{ cells} \times 10^4/\text{ml}$ of tracheal aspirate fluid, and total protein concentration below 400 µg/ml of tracheal aspirate fluid, such dosing being continued until the RDS, BDP, chronic lung disease and/or pulmonary fibrosis, asthma, or COPD has been treated, cured, or prevented.

These and other objects, features and advantages are also achieved by administering rhCC10 such that it does not inhibit platelet aggregation, suppress the immune response or increase the frequency or severity of adverse events.

In certain aspects of the invention, rhCC10 is administered intratracheally in a dose between about 1.5 and about 5.0 mg/kg of patient body mass or in multiple doses which taken together achieve this dosage range to treat, cure or prevent RDS, BDP, chronic lung disease and/or pulmonary fibrosis, asthma, or COPD. In another aspect, an rhCC10 dose or doses adding up to between about 1.5 and about 5.0 mg/kg of patient body mass may be repeated at appropriate intervals to treat, cure or prevent RDS, BDP, chronic lung disease and/or pulmonary fibrosis, asthma, or COPD. In yet other aspects of the invention, rhCC10 is administered intratracheally in accordance with the above aspects but in a dose or doses adding up to between about 15 nanograms/kg of patient body mass and about 10 mg/kg of patient body mass or in a dose adding up to between about 0.15 mg/kg and about 5 mg/kg of patient body mass. Whether administered intratracheally or otherwise, rhCC10 may be given alone, in conjunction with, before or after surfactant therapy.

DETAILED DESCRIPTION

Figure 1:
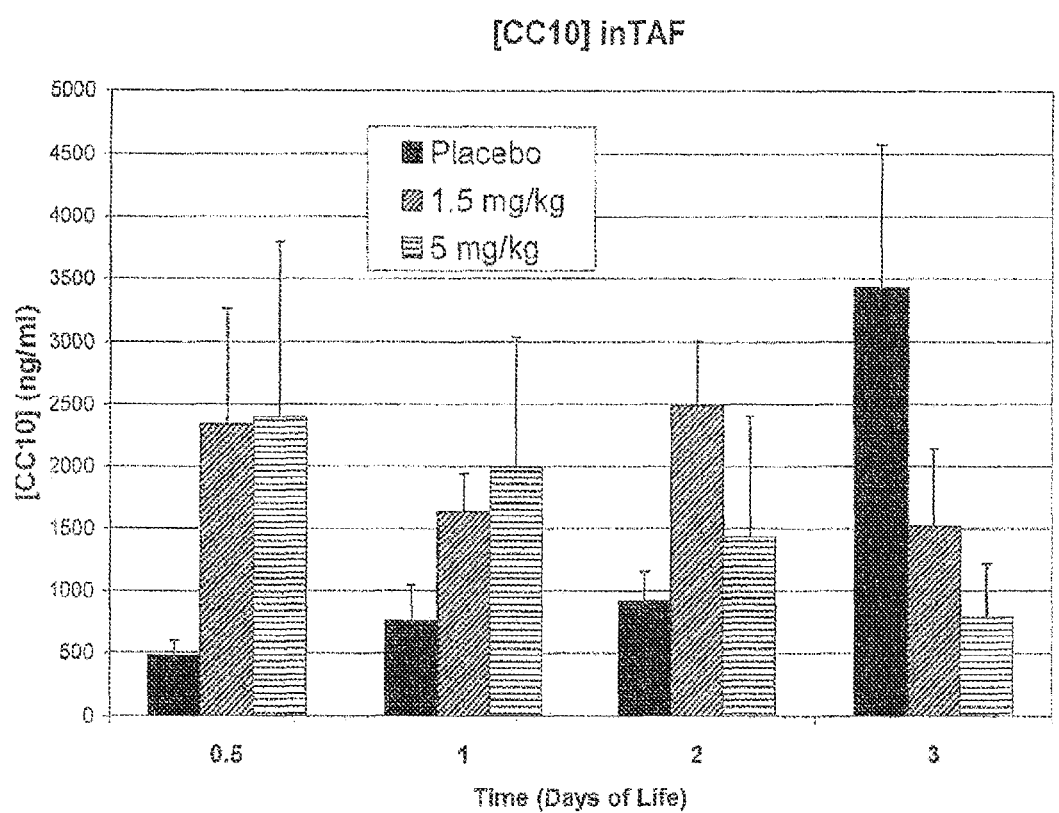
FIG. 1 is a bar graph of the CC10 concentration in the tracheal aspirate fluid of patients over time that were given placebo, rhCC10 at 1.5 mg/kg of body mass or rhCC10 at 5 mg/kg of body mass.

The present invention relates to the critical dosages and timing of administration of rhCC10 to treat, cure or prevent RDS, BDP, chronic lung disease and/or pulmonary fibrosis, asthma, and COPD in humans. rhCC10 is preferably obtained by the processes described in U.S. Patent Application Publication Nos. US 2003-0109429 and US 2003-0207795, both of which are incorporated by reference in their entirety, or via any other process which yields pharmaceutical grade rhCC10. The rhCC10 of the embodiments of the present invention may also be administered by the intratracheal, endotracheal, dialysate, ophthalmic, intravenous, systemic, or oral routes. Furthermore the rhCC10 of the embodiments of the present invention may be administered with, without, before or after surfactant therapy.

Preferably, in treating or preventing RDS or BPD rhCC10 is administered during the first day of an infant patient's life. More preferably, rhCC is administered as soon as medically possible during the first day of an infant patient's life, for example, and without limitation, within about 30 minutes of intubation and receipt of surfactant.

Premature infants are typically intubated for the purposes of administering oxygen and inflating their lungs, which would collapse without intubation. Intubation can then serve as a direct route for the intratracheal administration (also known as endotracheal administration) of medicines, such as surfactants, to the lungs. Thus the preferred route of administration for rhCC10 is also intratracheal administration, however alternate routes of administration are also possible such as inhalation, inhalation of pegylated rhCC10, injection into the muscle tissues, intravenous injection, intranasal administration, oral administration and administration by suppository.

rhCC10 may also be administered to treat, cure or prevent chronic lung disease and/or pulmonary fibrosis, asthma, and COPD. Based on the results described herein, rhCC10 will have therapeutic benefit to patients suffering from chronic lung disease and/or pulmonary fibrosis, asthma, and COPD. More specifically, and as shown below, rhCC10, when dosed at the amounts described below, lowers neutrophil counts, IL-6 levels and IL-8 levels in humans, and thus will provide an effective treatment for RDS, Asthma and COPD.

One method of measuring the therapeutic effect of rhCC10 on a patient is to measure conditions present in the tracheal aspirate fluid, which is indicative of conditions present in the tracheal and bronchoalveolar fluid of the patient's lungs. Such conditions may be one or more of the following: IL-6 levels, IL-8 levels, total neutrophil counts, total cell counts and total protein concentration.

A method of measuring the concentration of CC10 in a patient, and thus determining whether treatment has established therapeutically effective levels of CC10 in the patient, may include one or more of following: measuring CC10 concentration in TAF, serum or urine.

With reference to the following embodiments, rhCC10 may be administered to achieve certain desired effects, establishing that therapeutically effective levels of CC10 have been achieved in the patient, while at the same time avoiding other deleterious effects. For example, rhCC10 may be administered to achieve concentrations of CC10 in the tracheal aspirate fluid which exceed the deficient production of endogenous CC10 by the premature infant. rhCC10 may also be administered to achieve early peak serum concentrations of rhCC10 in patients, for example within about 6 hours after administration. As a further example, when administered in accordance with the described methods, rhCC10 administration may also achieve a peak concentration in urine at about 12 hours for example. As yet another example, rhCC10 may be administered so as to achieve significantly lower cell counts, neutrophil cell counts, protein concentrations, IL-6 levels and IL-8 levels in the patient's tracheal aspirate fluid and in the patient's lungs.

Furthermore, rhCC10 may be administered such that it does not significantly reduce the patient's endogenous CC10 production, inhibit platelet aggregation or cause an adverse immunologic reaction.

To effectuate the desired outcomes which are further described below, reference is made to methods of administration described in the following embodiments:

In one embodiment, a dose or multiple doses of rhCC10 equaling a dose ranging from about 1.5 to about 5 mg/kg of body mass may be administered. In another embodiment a dose or multiple doses of rhCC10 equaling a dose ranging from about 15 nanograms/kg of body mass to about 10 mg/kg of body mass is administered. In still another embodiment a dose or multiple doses of rhCC10 equaling a dose ranging from about 0.15 mg/kg and about 5 mg/kg of patient body mass is administered.

In yet another embodiment the above doses of rhCC10 may be administered intratracheally to the patient. In yet another embodiment, the above doses of rhCC10 may be administered to the patient by aerosol. In a further embodiment rhCC10, in accordance with the methods described above, may be administered prior to, during or after surfactant therapy. In still another embodiment, rhCC10, in accordance with the methods described above, may be administered to treat RDS, BPD, asthma, chronic lung disease, pulmonary fibrosis or COPD in a patient.

The doses of rhCC10 described above may be administered daily, more than once daily, every other day or in a tapered fashion depending upon the severity of disease being treated, the patient's overall health, and whether an acute or chronic condition is being treated. For example, the more severe the disease condition, a higher the amount of rhCC10 would be required to effectively treat the disease. For maintenance therapy of chronic disease, for example, to prevent an exacerbation of chronic Asthma, RDS, COPD, BDP or other pulmonary condition, lower doses would be required. It is understood that a physician would be able to monitor and adjust doses as needed based on the patient's symptoms and responses to therapy and within the parameters and dose ranges described in the embodiments of the present invention.

The following detailed examples are illustrations of embodiments. It should be clear that these are not intended to limit the scope of the present invention.

EXAMPLE 1

Administration of rhCC10 to Premature Infants

Patients were enrolled in a placebo-controlled, blinded, dose ranging study at four hospital sites.

rhCC10 was produced in *E. coli* bacteria and purified by a proprietary process (Claragen, Inc., College Park, Md.), described in U.S. Application Publication Nos. US 2003-0109429 and US 2003-0207795, both of which are incorporated by reference in their entirety. The protein for the study was provided as a >98% pure solution of recombinant human CC10 homodimer. The biological activity of each batch was compared using a proprietary secretory $PLA_2$ inhibition assay, described in U.S. Application Publication Nos. US 2002-0169108 which is incorporated herein by reference.

Newborn infants who met the following criteria were enrolled: 1) age≦24 h; 2) birth weight between 700 and 1,300 g; 3) gestational age≧24 wk; 4) diagnosis of RDS based on clinical and radiographic criteria; 5) requirement for intubation and mechanical ventilation; 6) receipt of surfactant, 100 mg/kg (Survanta, Ross Laboratory). Patients could be given subsequent doses of surfactant if clinically indicated following rhCC10 administration. Table 1 depicts the composition of the study groups (cohorts):

TABLE 1

Study Population

| | Gestational Age (weeks) | Birth Weight (grams) | Sex (Male/Total) | Race (White/Black/Hispanic/Asian) | Any Maternal Steroids |
|---|---|---|---|---|---|
| Placebo | 26.5 ± 1.6 | 943 ± 137 | 5/7 (71%) | 3, 2, 1, 1 | 7/7 |
| 1.5 mg/kg | 27.6 ± 1.2 | 981 ± 159 | 3/7 (43%) | 6, 2, 0, 0 | 6/7 |
| 5.0 mg/kg | 26.5 ± 1.2 | 878 ± 205 | 3/6 (50%) | 4, 2, 1, 0 | 6/6 | rhCC10, was formulated in a volume of 2 ml/kg of sterile, unbuffered saline. Patients were enrolled in two cohorts, each comparing study drug to placebo. The first cohort consisted of 12 patients, randomized so that one-third received placebo and the other two-thirds received rhCC10 at 1.5 mg/kg of body mass of the study drug. After the first cohort of patients was enrolled and the safety data reviewed by the DSMC, a second cohort of 12 patients was enrolled. They were also randomized so that one-third received placebo and the other two-thirds received rhCC10 at 5.0 mg/kg of body mass.

Each patient then received a single dose of the study drug (or placebo) as soon as possible after surfactant replacement therapy, but not longer than 4 h after surfactant. Study drug or placebo was administered intratracheally (IT) in two equal aliquots via a pre-measured feeding tube placed into the distal third of the endotracheal tube, with the patient in the right and then left lateral decubitus position and 30° of Trendelenburg.

As described in greater detail in Examples 2-4, pharmacokinetic analyses were conducted on samples of TAF, serum, and urine samples and analyses of cells counts and protein levels were performed on samples of TAF.

TAF was obtained by instilling 1 ml of saline into the endotracheal tube and suctioning the fluid into a Leuken's trap. The catheter was then washed with an additional 1 ml saline. In some cases the first tracheal aspirate was obtained prior to surfactant administration (baseline). Subsequent TAF collections were obtained at 12, 24, 48 and 72 hours post-administration. TAF was only collected if infants continued to require intubation and mechanical ventilation. The TAF was centrifuged at 300×g for 10 minutes to pellet the cells. The supernatant was removed and frozen at −70° C.

The pharmacokinetic analysis was conducted on samples of TAF, serum, and urine samples using a competitive ELISA for human CC10 developed by the sponsor. The assay utilizes a single anti-human CC10 polyclonal antibody as a capture reagent. CC10 in the sample competes with a synthetic CC10-HRP (horseradish peroxidase) conjugate for antibody binding sites in the plate wells. Thus, the signal decreases with increasing CC10 concentration in the sample. Samples were run in duplicate and a standard curve was run for each set of assays using rhCC10 calibrators. The limit of detection is 5 ng/ml and the results were reproducible with coefficients of variation typically under 20%. The assay does not appear to distinguish between native and recombinant CC10, thus total CC10 levels were measured. Immunogenicity of the study drug was assessed by titration of anti-C10 antibodies in serum obtained at 28 days post administration.

Referring to Examples 5-8 below, analyses for pulmonary inflammatory markers were performed as follows: The TAF cell pellet was resuspended and cell counts performed using a hemocytometer. Differential cell counts in TAF were determined by cytocentrifugation and differential staining. Total protein in TAF was measured using the Pierce BCA technique, and a panel of cytokines (Multiplex cytokine analysis, Luminetics Corp.) was measured in TAF from all three experimental groups at 0, 24 and 48 hours post-administration. IL-6 and IL-8 cytokines were measured in TAF from patients in all three groups at times 0, 1 and 2 days (with a minimum of three and maximum of seven samples/group).

Concentrations of CC10 and analysis of inflammatory markers over time were examined by using mixed model analysis of variance to test the interaction of time and dose. Non-parametric testing was performed when unequal variance was detected. Sample characteristics, the incidence of complications and clinical outcomes were analyzed by Fisher's Exact Test for categorical variables or one way analysis of variance for continuous variables.

EXAMPLE 2

TAF Concentrations of CC10 in Patients Treated with rhCC10

With reference to FIG. 1 it has been found that during the first 48 hours of life, after an initial dose of rhCC10, significantly increased overall CC10 concentration occurred in patients receiving rhCC10 in dosages comprising either 1.5 mg/kg of body mass or 5 mg/kg of body mass versus placebo. Thus, administration of rhCC10 during the first 24 hours of life has a significant positive impact on CC10 levels in patients during the first two days of life. Furthermore, administration of rhCC10 will increase overall CC10 concentrations in patients.

Reference is now made to Table 2, as well as to FIG. 1, the contents of which are further described in this example.

TABLE 2

| | Average TAF CC10 Concentrations | | | |
| --- | --- | --- | --- | --- |
| | CC10 Conc. in TAF** 12 Hours | CC10 Conc. in TAF 24 Hours | CC10 Conc. in TAF 48 Hours | CC10 Conc. in TAF 72 Hours |
| Placebo | 476 ng/ml | 753 ng/ml | 916 ng/ml | 3435 ng/ml |
| 1.5 mg/kg* rhCC10 | 2336 ng/ml | 1639 ng/ml | 2492 ng/ml | 1522 ng/ml |
| 5 mg/kg* rhCC10 | 2400 ng/ml | 1994 ng/ml | 1432 ng/ml | 784 ng/ml |

*dosage units are mg of rhCC10 per kg of patient body mass
**CC10 concentration in TAF are in units of ng of CC10 per ml of TAF CC10 concentrations in patients were measured at 12, 24, 48 and 72 hours post-administration. An average concentration for each patient group receiving a particular dose of rhCC10 (1.5 or 5 mg/kg) or placebo was determined as follows. CC10 concentrations in TAF were observed for time points where there were at least three patient samples per group (FIG. 1). This allowed for analysis of TAF samples for all groups following administration of placebo (0.9% sterile saline) or rhCC10 through day 3 of life. For safety and logistical reasons, samples were not obtained if surfactant had recently been administered or if the infant had been extubated. At 12 hours of life, CC10 concentrations in TAF from infants treated with the study drug was significantly higher than the placebo group, but there was little difference between the two groups who received rhCC10. Over the first 3 days of life, CC10 concentrations in TAF from infants receiving placebo generally increased, whereas CC10 levels in treated infants tended to remain constant (1.5 mg/kg of body mass) or decrease (5 mg/kg of body mass). However, CC10 levels from infants receiving placebo did not exceed the CC10 levels of those infants receiving rhCC10 in either 1.5 mg/kg of body mass or 5 mg/kg of body mass dosages during the first 48 hours of life. Those infants receiving 1.5 mg/kg of body mass rhCC10 had the highest levels of CC10 at 48 hours.

EXAMPLE 3

Serum Concentrations of CC10 in Patients Treated with rhCC10

Figure 2:
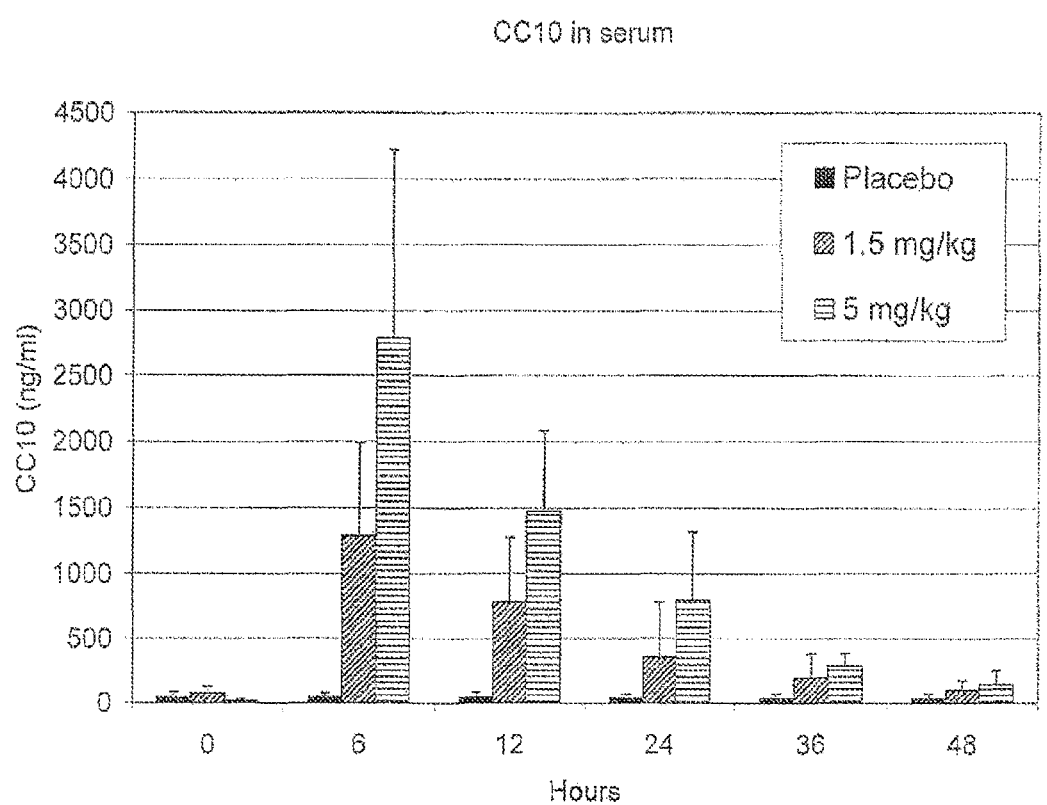
FIG. 2 is a bar graph of the CC10 concentration in the serum of patients over time that were given placebo, rhCC10 at 1.5 mg/kg of body mass or rhCC10 at 5 mg/kg of body mass.

Furthermore, with reference to FIG. 2, in one embodiment, rhCC10 may be administered intratracheally such that peak serum levels of CC10 are achieved within 6 hours of administration. Peak serum levels occur within 6 hours, irrespective of the dose of rhCC10 administered. Based on the results described below and in FIG. 2, peak serum levels will occur within about 6 hours after administration across all dosage ranges.

Reference is now made to Table 3, as well as to FIG. 2, the contents of which are further described in this example.

TABLE 3

Average Serum CC10 Concentrations

|  | CC10 Conc. in serum** 0 Hours | CC10 Conc. in serum** 6 Hours | CC10 Conc. in serum** 12 Hours | CC10 Conc. in serum** 24 Hours | CC10 Conc. in serum** 36 Hours | CC10 Conc. in serum** 48 Hours | Elimination Half-life |
|---|---|---|---|---|---|---|---|
| Placebo | 42 ng/ml | 43 ng/ml | 46 ng/ml | 40 ng/ml | 37 ng/ml | 38 ng/ml | Not applicable |
| 1.5 mg/kg* rhCC10 | 76 ng/ml | 1289 ng/ml | 782 ng/ml | 354 ng/ml | 196 ng/ml | 101 ng/ml | 11.6 hours |
| 5 mg/kg* rhCC10 | 22 ng/ml | 2794 ng/ml | 1476 ng/ml | 798 ng/ml | 290 ng/ml | 143 ng/ml | 9.9 hours |

*dosage units are mg of rhCC10 per kg of patient body mass
**CC10 concentration in serum are in units of ng of CC10 per ml of serum In determining average peak serum levels, blood (0.3 ml) was obtained for the measurement of serum concentration of CC10 before drug administration (0 hours) and at 6, 12, 24, 36, and 48 hours after administration of rhCC10. An average concentration for each patient group receiving a particular dose of rhCC10 or placebo was determined.

Serum concentrations of CC10 were similar in all 3 groups before treatment (FIG. 2). Infants who received rhCC10 had substantially higher serum concentrations than infants receiving placebo and this varied in a dose dependent manner. Average peak serum levels after administration of rhCC10 may range from about 1290 ng/ml of serum to about 2800 ng/ml serum when rhCC10 is given in a single dose of between 1.5 mg/kg of body mass and 5 mg/kg of body mass. As shown in Table 3, the elimination half-life of a rhCC10 dosage of 1.5 mg/kg of body mass was about 11.6 hours, whereas the elimination half-life of a rhCC10 dose of 5 mg/kg of body mass was about 9.9 hours. CC10 concentrations in the serum of treated infants were comparable to placebo levels within 48 hours of administration.

EXAMPLE 4

Urine Concentrations of CC10 in Patients Treated with rhCC10

Figure 3:
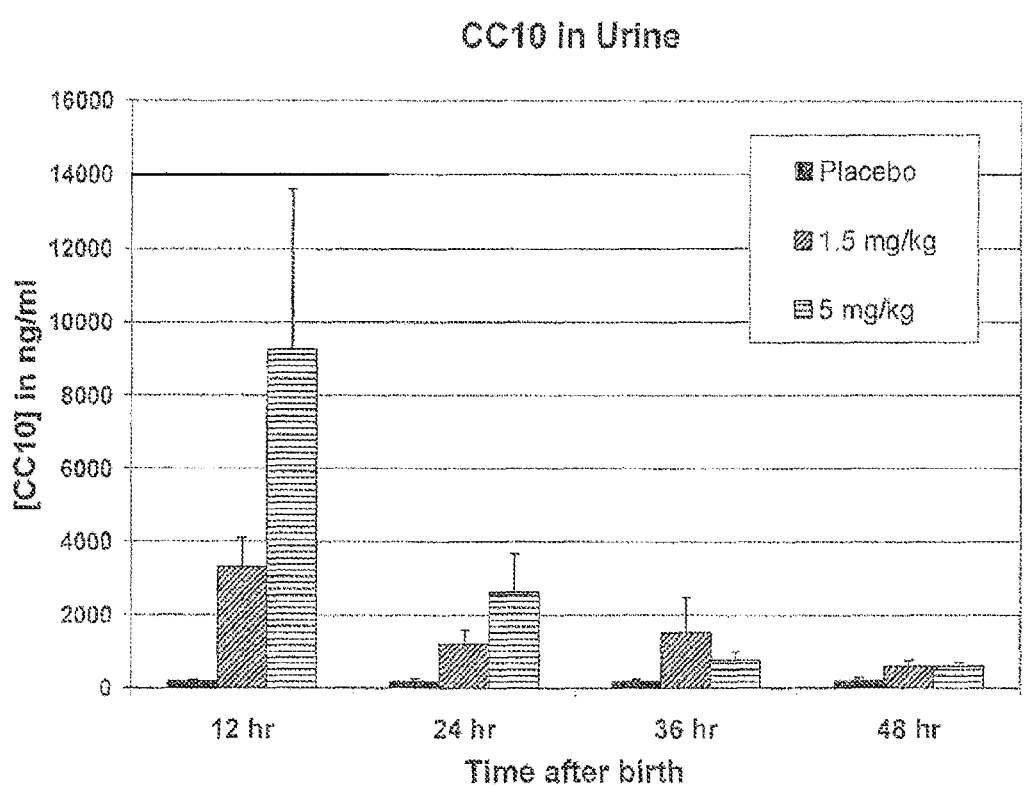
FIG. 3 is a bar graph of the CC10 concentration in the urine of patients over time who were given placebo, rhCC10 at 1.5 mg/kg of body mass or rhCC10 at 5 mg/kg of body mass.

Referring to FIG. 3, in one embodiment, rhCC10 may also be administered intratracheally at the above-mentioned dosages such that peak CC10 levels in urine occur 12 hours after administration. For example, CC10 concentrations in the urine of treated infants increase in a largely dose-dependent manner, but are comparable to placebo levels within 48 h of administration.

Reference is now made to Table 4, as well as to FIG. 3, the contents of which are further described in this example.

TABLE 4

Average Urine CC10 Concentrations

|  | CC10 Conc. in urine** 12 Hours | CC10 Conc. in urine** 24 Hours | CC10 Conc. in urine** 36 Hours | CC10 Conc. in urine** 48 Hours |
|---|---|---|---|---|
| Placebo | 197 ng/ml | 183 ng/ml | 180 ng/ml | 203 ng/ml |
| 1.5 mg/kg* rhCC10 | 3312 ng/ml | 1226 ng/ml | 1513 ng/ml | 593 ng/ml |
| 5 mg/kg* rhCC10 | 9239 ng/ml | 2613 ng/ml | 763 ng/ml | 583 ng/ml |

*dosage units are mg of rhCC10 per kg of patient body mass
**CC10 concentration in serum are in units of ng of CC10 per ml of urine Urine samples were obtained at 12, 24, 36 and 48 hours after administration of rhCC10. Each urine sample consisted of the total volume voided over the previous 12 hours.

In urine, CC10 concentrations in treated infants increased in a largely dose-dependent manner, but were comparable to placebo levels within 48 h of administration (FIG. 3).

EXAMPLE 5

Total Cell Counts in TAF of Patients Treated with rhCC10

Figure 4:
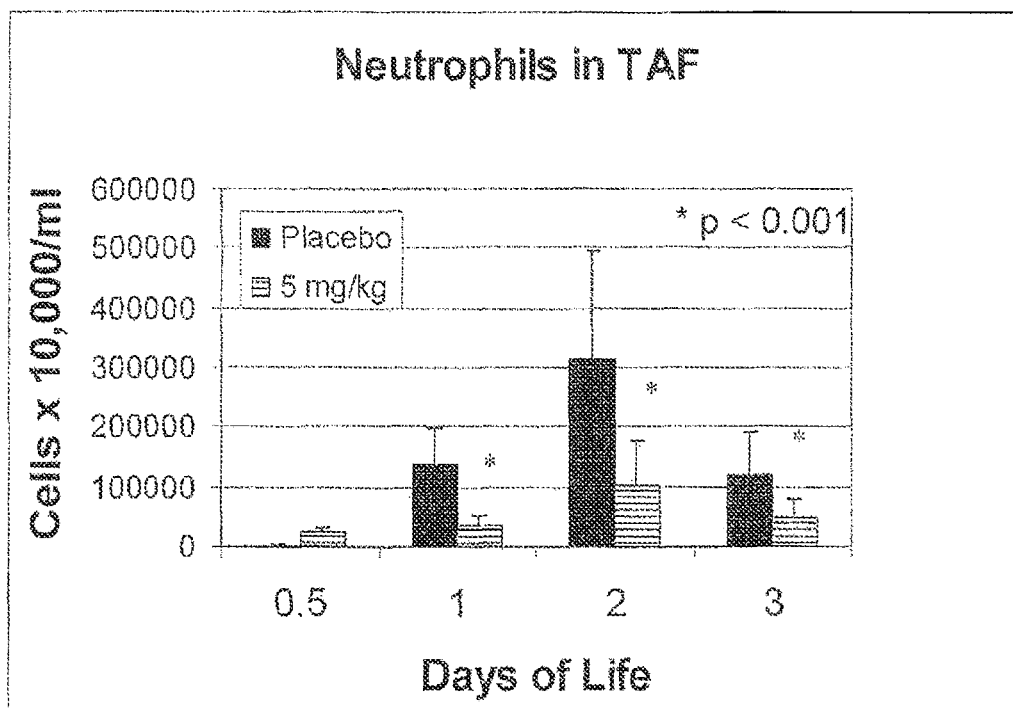
FIG. 4 is a bar graph of total cell counts in the tracheal aspirate fluid of patients over time who were given placebo, or rhCC10 at 5 mg/kg of body mass.
Figure 5:
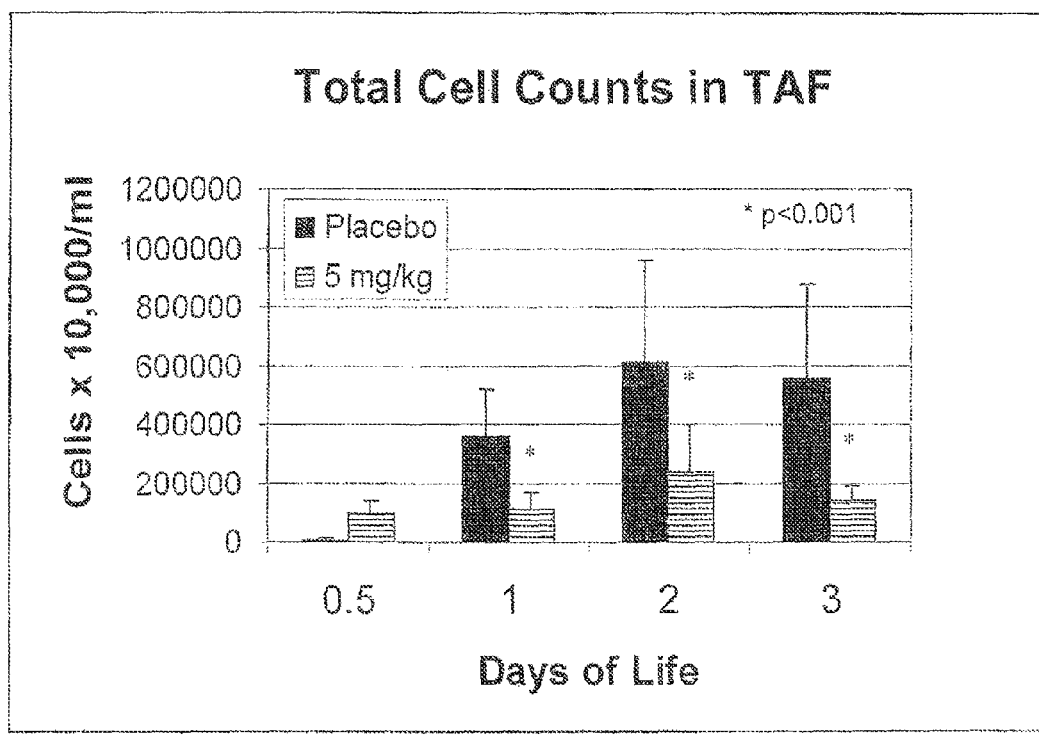
FIG. 5 is a bar graph of total neutrophil counts in the tracheal aspirate fluid of patients over time who were given placebo or rhCC10 at 5 mg/kg of body mass.

As shown in FIG. 4 and in Table 5, total cell counts were performed on TAF fluids and are shown in FIG. 5. Average total cell counts were obtained by measuring and averaging total cell counts in TAF within the placebo and 5 mg/kg rhCC10 study groups. Study groups were sampled at 0.5, 1, 2, and 3 days post-administration.

TABLE 5

Total Cell Counts in TAF

|  | Total cell count** 0.5 days | Total cell count** 1 day | Total cell count** 2 days | Total cell count** 3 days |
|---|---|---|---|---|
| Placebo | 1.0 | 36 | 61 | 56 |
| 5 mg/kg* rhCC10 | 9.8 | 11 | 24 | 14 |

*dosage units are mg of rhCC10 per kg of patient body mass
**total cell counts are in units of Cells × $10^4$ per ml of TAF Total cell counts were significantly lower in the 5 mg/kg group on days 1-3 compared to the placebo group. Total cells counts were at least twice as low during days 1-3 of life after rhCC10 at 5 mg/kg of body mass was administered versus placebo.

EXAMPLE 6

Total Neutrophil Counts in TAF in Patients Treated with rhCC10

Total neutrophil counts were performed on TAF fluids in order to gauge rhCC10's effect on inflammation in the lungs and are shown in FIG. 5. Inflammation of the lungs is caused by an excess of neutrophil cells which are a cause of RDS, BDP, chronic lung disease, pulmonary fibrosis, asthma, and COPD. Average neutrophil counts were obtained by measuring and averaging neutrophil counts in TAF within each study group (placebo and 5 mg/kg rhCC10). Study groups were sampled at 0.5, 1, 2, and 3 days post-administration.

TABLE 6

Total Neutrophil Counts in TAF

|  | Total cell count** 0.5 days | Total cell count** 1 day | Total cell count** 2 days | Total cell count** 3 days |
|---|---|---|---|---|
| Placebo | 0.1 | 13.7 | 31.2 | 12 |
| 5 mg/kg* rhCC10 | 2.4 | 3.4 | 10.2 | 4.7 |

*dosage units are mg of rhCC10 per kg of patient body mass
**total cell counts are in units of Cells × $10^4$ per ml of TAF Neutrophil counts were significantly lower in the 5 mg/kg group relative to the placebo group. For example, on day two the placebo group's neutrophil levels were over 30 cells×10(4)/ml of TAF versus about 10 cells×10(4)/ml of TAF for the group receiving rhCC10 at 5 mg/kg of body mass. Therefore, excessive neutrophil cell amounts were minimized in the lungs.

EXAMPLE 7

Total Protein Concentration in TAF of Patients Treated with rhCC10

Figure 6:
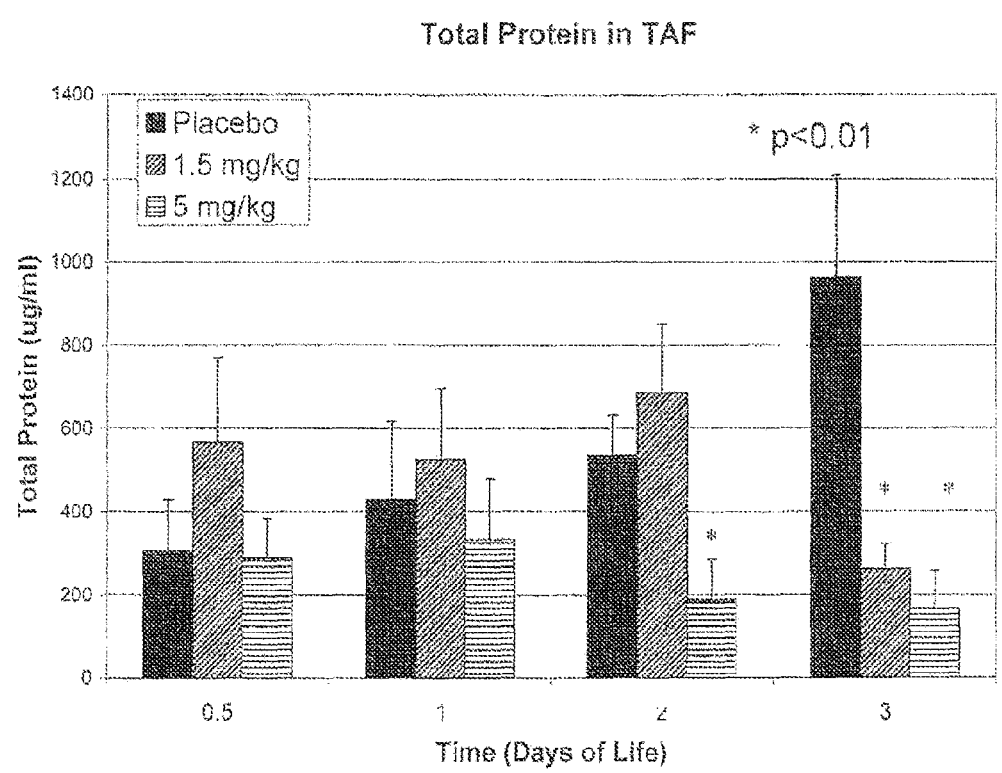
FIG. 6 is a bar graph of total protein concentration in the tracheal aspirate fluid of patients over time who were given placebo, rhCC10 at 1.5 mg/kg of body mass or rhCC10 at 5 mg/kg of body mass.

Referring now to FIG. 6 and to Table 7, total protein levels were measured in the TAF of both treatment groups (rhCC10 at 1.5 mg/kg and 5 mg/kg of body mass) in order to gauge rhCC10's effect on protein leak and pulmonary edema. Both protein leak and pulmonary edema are conditions damaging to the lungs and symptomatic of RDS, BDP, chronic lung disease, pulmonary fibrosis, asthma, and COPD. Average total protein concentrations were obtained by measuring and averaging total protein concentrations in TAF within each study group (placebo, 1.5 mg/kg rhCC10 and 5 mg/kg rhCC10). Study groups were sampled at 0.5, 1, 2, and 3 days post-administration.

TABLE 7

Total Protein Concentrations in TAF

|  | Total protein conc.** 0.5 days | Total protein conc.** 1 day | Total protein conc.** 2 days | Total protein conc.** 3 days |
|---|---|---|---|---|
| Placebo | 307 | 430 | 536 | 964 |
| 1.5 mg/kg* rhCC10 | 565 | 527 | 685 | 264 |
| 5 mg/kg* rhCC10 | 289 | 334 | 189 | 167 |

*dosage units are mg of rhCC10 per kg of patient body mass
**total cell counts are in units of µg of protein per ml of TAF Total protein was significantly lower in TAF from both treatment groups compared to placebo. For example, by day three post-administration, total protein in the TAF of the placebo group was nearly 1000 µg/ml of TAF whereas total protein in the treatment groups on day three did not exceed 350 µg/ml of TAF. Thus protein leak and pulmonary edema had been minimized in the treatment groups.

EXAMPLE 8

Total IL-6 Levels in TAF CC10 in Patients Treated with rhCC10

IL-6 cytokine was measured in TAF from patients in all three groups at times 0, 1 and 2 days post-administration (with a minimum of three and maximum of seven samples/group).

Figure 7:
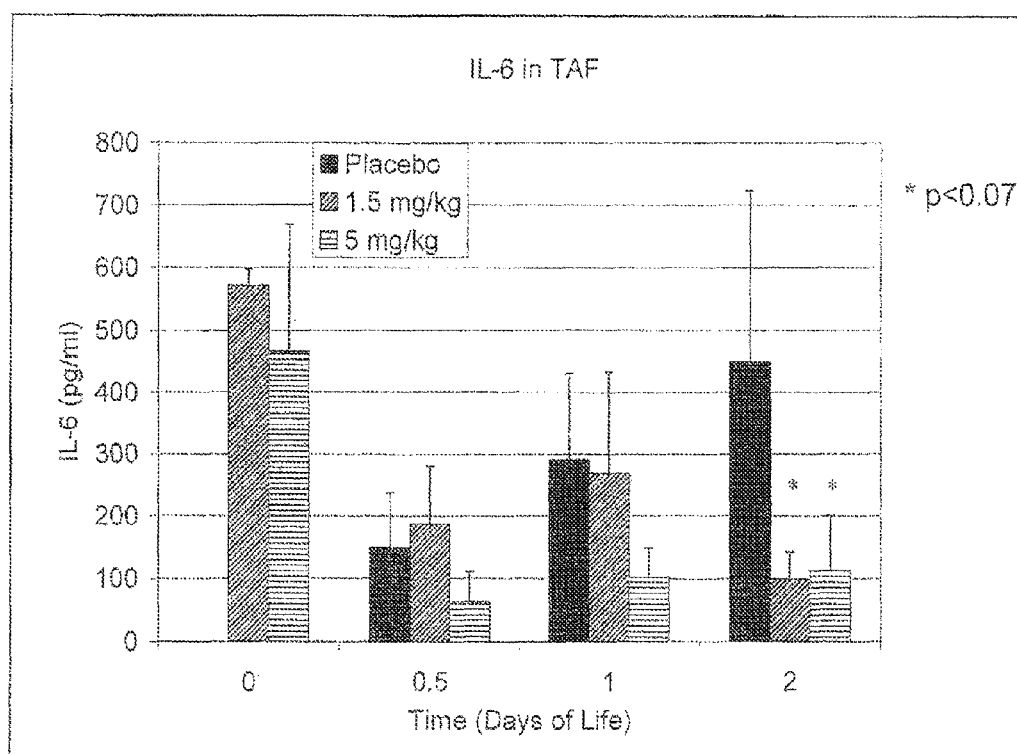
FIG. 7 is a bar graph of 1L-6 levels in the tracheal aspirate fluid of patients over time who were given placebo, rhCC10 at 1.5 mg/kg of body mass or rhCC10 at 5 mg/kg of body mass.

Referring now to Table 8 and FIG. 7, IL-6 concentrations were effectively reduced by the study drug (rhCC10 in saline) in both groups, but increased over time in the placebo group.

TABLE 8

Pharmacokinetic Results: IL-6 Levels in TAF

|  | IL-6 level 0 days | IL-6 level** 0.5 days | IL-6 level** 1 day | IL-6 level** 2 days |
|---|---|---|---|---|
| Placebo | n/a | 150 | 291 | 449 |
| 1.5 mg/kg* rhCC10 | 572 | 187 | 269 | 99 |
| 5 mg/kg* rhCC10 | 446 | 64 | 103 | 113 |

*dosage units are mg of rhCC10 per kg of patient body mass
**total cell counts are in units of pg of IL-6 per ml of TAF For example, those patients receiving rhCC10 at 5 mg/kg of body mass had IL-6 levels below 200 pg/ml of TAF over the first two days following administration. Those patients receiving rhCC10 at 1.5 mg/kg of body mass had IL-6 levels below 300 pg/ml of TAF over the first two days post-administration and had an IL-6 level below 100 pg/ml by day two. However, those patients on placebo had steadily increasing IL-6 levels, exceeding 400 pg/ml by day 2. Thus rhCC10, when administered according to the present teachings, reverses the upward trend of IL-6 levels in patient lungs, thus preventing neutrophil influx to the lung.

EXAMPLE 9

Total IL-8 Levels in TAF and Serum in Patients Treated with rhCC10

Figure 8:
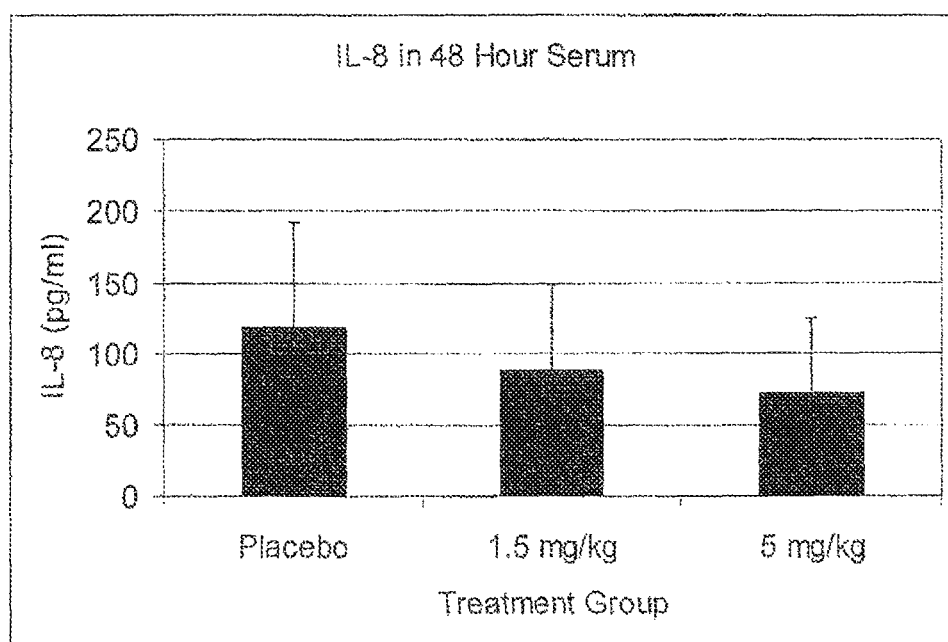
FIG. 8 is a bar graph of IL-8 levels in the serum of patients at 48 hours after administration who given placebo, rhCC10 at 1.5 mg/kg of body mass or rhCC10 at 5 mg/kg of body mass.

Referring now to FIG. 8 and Table 9, IL-8 cytokine was measured in TAF from patients in all three groups at 48 hours post-administration. IL-8 is a potent chemoattractant for neutrophils and other circulating inflammatory cells, that is released by local epithelial cells, resident immune cells, and fibroblasts in response to injury or irritation.

TABLE 9

Pharmacological Results: Total IL-8 Levels in Serum

|  | IL-8 in Serum** 48 hours |
|---|---|
| Placebo | 118 pg/ml |
| 1.5 mg/kg* rhCC10 | 89 pg/ml |
| 5 mg/kg* rhCC10 | 72 pg/ml |

*dosage units are mg of rhCC10 per kg of patient body mass
**total IL-8 levels are in units of pg of IL-8 per ml of serum IL-8 levels were lower in rhCC10-treated patients than in patients receiving placebo. Administration of rhCC10, as depicted above, reduced the levels of IL-8 released from the lungs and into the systemic circulation. Thus, this data shows that rhCC10 is effective at treating or preventing RDS, BDP, chronic lung disease and/or pulmonary fibrosis, asthma, and COPD by lowering IL-8 levels and thus treating the causative agent of these diseases.

EXAMPLE 10

Outcomes

Table 10 depicts comparative outcomes of patients who received rhCC10 versus patients who received placebo.

Patients were monitored at six months of corrected age (the developmental timepoint at which they would have been six months old had they been born at the normal 40 weeks of gestation.) Table 11 depicts further comparative outcomes of patients who received rhCC10 versus patients who received placebo.

TABLE 10

Outcomes at 6 Month Corrected Age

| Outcome | Placebo | 1.5 mg/kg | 5 mg/kg |
|---|---|---|---|
| # with repeat Respiratory symptoms (cough, wheezing) | 4/6 | 4/6 | 0/5 |
| # with doctor visits for Respiratory symptoms | 4/6 | 2/6 | 3/5 |
| # hospitalized for breathing problems | 3/6 | 0/6 | 0/5 |

Referring to Table 10 above, patients who received rhCC10 therapy had reduced incidences of respiratory symptoms, e.g. coughing and wheezing. Coughing and wheezing are symptoms common RDS, BDP, chronic lung disease and/or pulmonary fibrosis, asthma, and COPD. After receiving rhCC10, patients had fewer doctor visits due to respiratory symptoms, and no patients were hospitalized for breathing problems in comparison to 50% of infants in the placebo group who were hospitalized for their respiratory symptoms. This data shows that rhCC10 significantly reduces the severity of respiratory symptoms, preventing the need for rehospitalization.

TABLE 11

Observations During Initial Hospitalization

| | Placebo | 1.5 mg/kg | 5 mg/kg |
|---|---|---|---|
| Doses of Surfactant | 1.9 +/− 10.7 | 1.4 +/− 0.7 | 1.5 +/− 0.5 |
| Days on Ventilator | 12.1 ± 8.6 | 8.2 ± 7.8 | 24 ± 13.1 |
| Days on Ventilator and NCPAP | 33 ± 12.7 | 18.7 ± 13.2* | 44.3 ± 18.1 |
| Days on $O_2$ | 56.6 ± 13.1 | 49 ± 11.2 | 55 ± 18.1 |
| $O_2$ at 28 d | 7/7 | 7/7 | 5/6 |
| $O_2$ at 36 wk PCA | 2/7 | 1/7 | 3/6 |
| Hospitalized at 36 wk PCA | 5/7 (71.4%) | 2/7 (28.6%) | 4/6 (66.7%) |
| PDA | 5/7 | 3/8 | 2/7 |
| Sepsis | 0/0 | 1/8 | 1/7 |
| IVH | 2/7 | 0/8 | 1/7 |
| PVL | 1/7 | 0/8 | 0/7 |

NCPAP - nasal continuous positive airway pressure,
NEC - necrotizing enterocolitis;
PCA - post-conceptual age,
PDA - patent ductus arteriosus,
IVH - intraventricular hemorrhage,
PVL - periventricular leukomalacia Referring to Table 11 above, the therapeutic effect of rhCC10 on short term respiratory distress is reflected in the decreased requirement for additional doses of exogenous surfactant therapy. The length of hospital stays was tabulated for each study group. Only 28.6% of patients in the low dose group were still hospitalized after 36 weeks compared to 71.4% of patients in the placebo group and 66.7% in the high dose groups.

Patients in the low dose rhCC10 group (1.5 mg/kg of body mass) were on the ventilator and NCPAP for significantly fewer days than the placebo patients. When total days of mechanical ventilation were evaluated, there was also a trend towards a reduction in the need for ventilatory support in the low dose group (the 1.5 mg/kg body mass group).

These results show that rhCC10 therapy, when administered in accordance with the present teachings, decreased the severity of RDS compared to placebo and reduced or eliminated the incidence of respiratory problems severe enough to warrant medical attention or rehospitalization.

Furthermore, this data shows that the safety profile of rhCC10 is superior to other anti-inflammatory agents such as corticosteroids. The safety and tolerability of the study drug were assessed through 36 weeks PCA (Post conceptual age, also known as PMA—post menstrual age) by comparing the incidence of adverse events in the treatment and placebo groups and to the historical incidence of the adverse events at each institution. No deaths were attributable to administration of rhCC10.

In addition, a preliminary assessment of the efficacy of IT rhCC10 in decreasing the incidence of BPD was made on the basis of the following data: duration of mechanical ventilation, oxygen requirement at 28 days with an abnormal chest radiograph, oxygen requirement at 36 weeks PCA or date of discharge.

Growth parameters were assessed at birth, 28 days of age and 36 weeks PCA. Blood chemistries and liver function tests were evaluated at the onset of the study and on days 7 and 28 post-administration. Complete blood counts and urinalysis were performed on enrollment, 24, 48 and 72 h, 7 and 28 d post-administration. Cranial ultrasounds were performed upon randomization and were repeated at 7 and 28 d of life.

EXAMPLE 12

Incidence of PVL and IVH Adverse Events

There were no instances of PVL. (peri-ventricular leukomalacia) in the rhCC10-treated infants. However, there was one infant in the placebo group who developed PVL. PVL occurs when leukocytes (primarily neutrophils) infiltrate the brain and cause a severe inflammatory response. PVL, if not lethal, typically results in severe neurological impairment in the infant. Smaller and younger infants are predisposed to PVL. Even though the infants in the high dose group (5.0 mg/kg patient body mass) were smaller and younger than in the placebo group,there was no PVL in the high dose group. rhCC10 thus protected these disadvantaged infants from PVL.

Likewise, the incidence of IVH (Intraventricular hemorrhage), which occurs when a blood vessel in the brain bursts in response to aggressive ventilation and high oxygen levels, was lower in the rhCC10 treated groups than in the placebo group. RhCC10 appears to have protected these disadvantaged infants in the high dose group from IVH, refuting the scientific papers that taught that rhCC10 inhibits platelet aggregation and would promote hemorrhaging in vivo.

PDA (patent ductus arteriosis), a defect or incomplete closure in the walls of the heart, was significantly decreased in the rhCC10-treated groups compared to placebo. PDA is a life-threatening problem that must be corrected surgically, if it is not resolved in the first several months of life. rhCC10 reduced the incidence of PDA, possibly by decreasing the stress on the heart.

There were no significant differences in values obtained for blood chemistries, complete blood counts or results of urinalysis among groups at any of the time points evaluated.

There were no significant differences in the incidence of non-respiratory adverse events in the treatment and placebo groups (Table 2). Three cases of NEC occurred at one center in rhCC10-treated infants. However, other premature infants not enrolled in the study at that center also developed NEC at the same time. Growth parameters were similar among the groups.

EXAMPLE 13

Immunological Safety

It will be further appreciated that the safety of rhCC10 can be measured by conducting an analysis of the potential immunogenicity of the administered rhCC10 using plasma samples. Plasma samples collected on day 28 of life were tested for the presence of anti-CC10 antibodies. No evidence of antibody formation was present in any of the 28 day plasma samples from any of the groups.

EXAMPLE 14

Other Outcomes

With reference to Table 2, there were no significant differences in the incidence of non-respiratory adverse events in the treatment and placebo groups. Three cases of NEC occurred at one center in rhCC10-treated infants. However, other premature infants not enrolled in the study at that center also developed NEC at the same time. Growth parameters at 36 weeks CGA were similar among the groups. Similarly, there were no significant differences in values obtained for blood chemistries, complete blood counts or results of urinalysis among groups at any of the time points evaluated. Thus, rhCC10 administration, in contrast to corticosteroids, did not appear to cause any significant safety issues in premature infants.

In addition, IT rhCC10 did not elicit an immunogenic response from treated infants. The only adverse event that was increased in treated infants compared to placebo controls was NEC (p=NS), however, it was not possible to attribute the NEC to the administration of rhCC10 for two reasons. First, excess CC10 was cleared from all infants by 48 h post-administration and the 3 cases of confirmed NEC occurred 3-6 wk post-administration. Second, all cases of confirmed NEC occurred at the same center. In addition, there were other cases of NEC in infants not enrolled in the rhCC10 study in this center occurring in the same timeframe, suggesting an outbreak pattern. These data indicate it is highly unlikely that rhCC10 administration was related to the development of NEC.

Referring now to, for example, Examples 10-13, it has been shown that rhCC10 is safe and well-tolerated because, upon administration to a patient, it does not elicit any immediate or delayed local or systemic reactions in the patient, it is not associated with any unusual adverse events, or increased severity or frequency of typical adverse events for the treated patient population, as described above. Furthermore, rhCC10 is safe and well-tolerated because it does not elicit any immunologic response from the patient to either the rhCC10 or to endogenous CC10, does not predispose the patient to bleeding or hemorrhage, or specifically increase the platelet aggregation time in the patient, and does not compromise the patient's immune function and predispose the patient to infection.

EXAMPLE 15

A patient, who may be an adult, child or a premature infant presents with RDS, BDP, chronic lung disease (in the case of a child or an adult), pulmonary fibrosis (in the case of a child or an adult), asthma, or COPD. A dose of rhCC10 from 1.5 mg/kg to 5 mg/kg of patient body mass is given to the patient. The patient will then demonstrate a resolution of the symptoms of the aforementioned condition.

EXAMPLE 16

A patient, who may be an adult, child or a premature infant presents with RDS, BDP, chronic lung disease (in the case of a child or an adult), pulmonary fibrosis (in the case of a child or an adult), asthma, or COPD. A dose of rhCC10 from 0.15 ng/kg to 5 mg/kg of patient body mass is given to the patient. The patient will then be relieved of the symptoms of the aforementioned condition.

EXAMPLE 17

A patient, who may be an adult, child or a premature infant presents with RDS, BDP, chronic lung disease (in the case of a child or an adult), pulmonary fibrosis (in the case of a child or an adult), asthma, or COPD. A dose of rhCC10 from 0.15 mg/kg to 5 mg/kg of patient body mass is given to the patient. The patient will then be relieved of the symptoms of the aforementioned condition.

Based on the foregoing, the critical ranges for rhCC10 dosages effective to safely treat, cure and prevent RDS, BDP, chronic lung disease and/or pulmonary fibrosis, asthma, and COPD have been found. Accordingly, the present invention provides a safe and well-tolerated rhCC10 based therapy effective at treating the symptoms of RDS, BDP, chronic lung disease and/or pulmonary fibrosis, asthma, and COPD thus increasing the long term survivability of both premature infants, child and adult patients suffering from these conditions, while not causing any dangerous side effects.

The invention claimed is:

1. A method of reducing total protein concentration in the tracheal fluid of a patient in need thereof comprising: administering a therapeutically effective amount of rhCC10 to the patient,
wherein the rhCC10 is administered by the intratracheal, endotracheal, dialysate, ophthalmic, intravenous, systemic, or oral routes and total protein concentration in the patient's tracheal fluid is reduced.

2. The method of claim 1 wherein between about 15 ng to about 10 mg rhCC10 per kg of patient body mass is administered.

3. The method of claim 1 wherein between about 0.15 mg to about 5 mg rhCC10 per kg of patient body mass is administered.

4. The method of claim 1 wherein between about 1.5 mg and about 5 mg rhCC10 per kg of patient body mass is administered.

5. The method of claim 1 further comprising the step of measuring the patient's IL-8 serum levels wherein the patient's serum 1L-8 level is less than 120 pg/ml after administration.

6. The method of claim 1 further comprising the step of measuring the patient's serum or urine CC10 levels wherein the patient has a serum concentration of CC10 of about 100 ng/ml of serum to 2800 ng/ml of serum or a urine concentration of CC10 of about 100 ng/ml to about 10,000 ng/ml during treatment.

7. The method of claim 1 further comprising the step of measuring the patient's serum CC10 levels wherein the patient's peak serum concentration of CC10 is about 1280 ng/ml of serum to about 2800 ng/ml of serum after administration.

8. The method of claim 1 further comprising the step of measuring the patient's serum CC10 levels wherein a peak serum concentration of CC10 is reached within about 6 hours after initial dosage.

9. The method of claim 1 further comprising the step of measuring the patient's tracheal aspirate fluid CC10 levels wherein the patient reaches a peak tracheal aspirate fluid concentration of CC10 between about 12 and about 48 hours after initial dosage.

10. The method of claim 1 wherein the administration of rhCC10 is repeated at least once on a 48 hour interval.

* * * * *